(12) United States Patent
Brown et al.

(10) Patent No.: US 6,632,626 B1
(45) Date of Patent: *Oct. 14, 2003

(54) METHODS OF ASSAYING FARNESYL TRANSFERASE

(75) Inventors: Michael S. Brown, Dallas, TX (US); Joseph L. Goldstein, Dallas, TX (US); Yuval Reiss, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/665,362

(22) Filed: Sep. 19, 2000

Related U.S. Application Data

(60) Division of application No. 07/937,893, filed on Dec. 22, 1992, which is a continuation-in-part of application No. 07/615,715, filed on Nov. 20, 1990, now Pat. No. 5,141,851, which is a continuation-in-part of application No. 07/510,706, filed on Apr. 18, 1990, now abandoned.

(51) Int. Cl.⁷ .................................................. C12Q 1/48
(52) U.S. Cl. ..................... 435/15; 435/69.2; 435/193; 536/23.2
(58) Field of Search .................. 435/15, 69.2, 193; 530/335; 536/23.2

(56) References Cited

U.S. PATENT DOCUMENTS

| | | | | |
|---|---|---|---|---|
| 5,141,851 A | * | 8/1992 | Brown et al. ................... | 435/15 |
| 5,238,922 A | * | 8/1993 | Graham et al. ................ | 514/18 |
| 5,420,245 A | * | 5/1995 | Brown et al. ................ | 530/328 |
| 5,532,359 A | * | 7/1996 | Marsters et al. ............. | 540/522 |
| 5,843,941 A | * | 12/1998 | Marsters et al. ............. | 514/221 |
| 5,856,310 A | * | 1/1999 | Sebti et al. .................... | 514/19 |
| 5,962,243 A | * | 10/1999 | Brown et al. .................. | 435/15 |
| 5,976,851 A | * | 11/1999 | Brown et al. ................. | 435/193 |
| 6,083,917 A | * | 7/2000 | Brown et al. .................. | 514/18 |

OTHER PUBLICATIONS

Dudley M. Biosynthesis of the Macrocyclic Diterpene Casbene in Castor Bean Seedlings. Plant Physiology (1986)81:343–348.*

* cited by examiner

Primary Examiner—Ralph Gitomer
(74) Attorney, Agent, or Firm—Fulbright & Jaworski L.L.P.

(57) ABSTRACT

Disclosed are methods and compositions for the identification, characterization and inhibition of farnesyl protein transferases, enzymes involved in the farnesylation of various cellular proteins, including cancer related ras proteins such as $p21^{ras}$. One farnesyl protein transferase which is disclosed herein exhibits a molecular weight of between about 70,000 and about 100,000 upon gel exclusion chromatography. The enzyme appears to comprise one or two subunits of approximately 50 kDa each. Methods are disclosed for assay and purification of the enzyme, as well as procedures for using the purified enzyme in screening protocols for the identification of possible anticancer agents which inhibit the enzyme and thereby prevent expression of proteins such as $p21^{ras}$. Also disclosed is a families of compounds which act either as false substrates for the enzyme or as pure inhibitors and can therefore be employed for inhibition of the enzyme. The most potent inhibitors are ones in which phenylalanine occurs at the third position of a tetrapeptide whose amino terminus is cysteine.

7 Claims, 12 Drawing Sheets

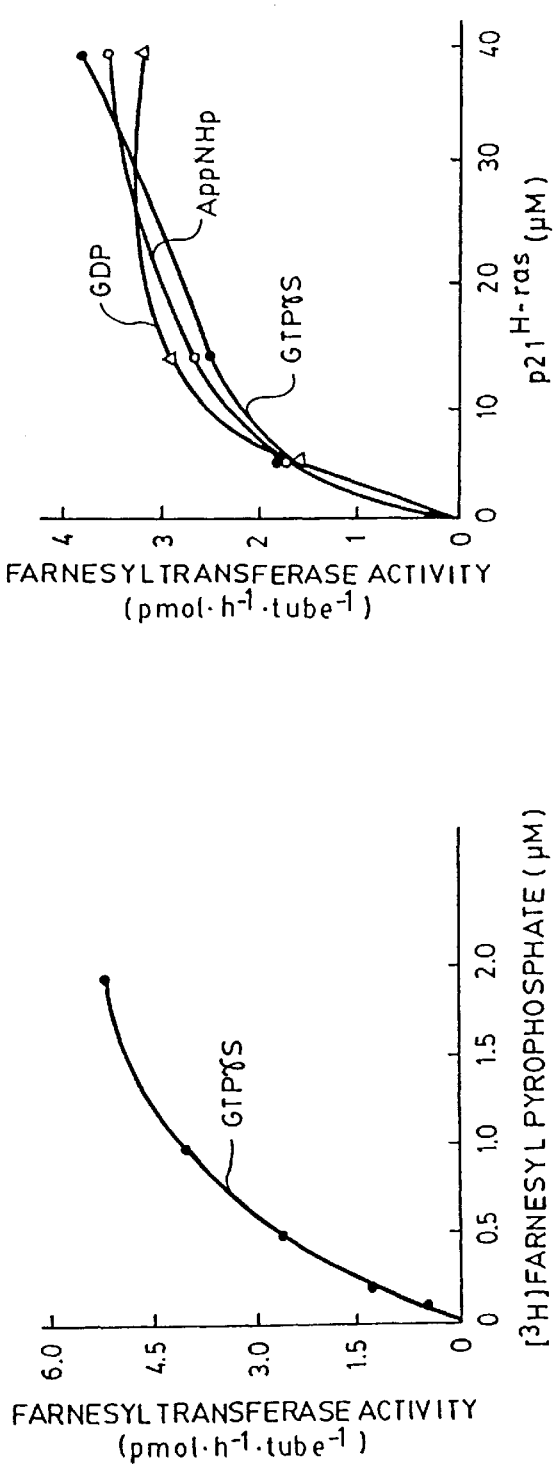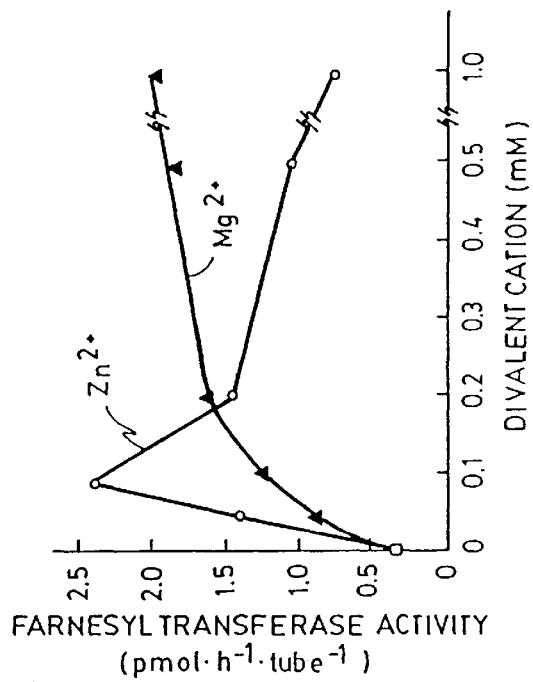
FIG. 2B
FIG. 3
FIG. 2A

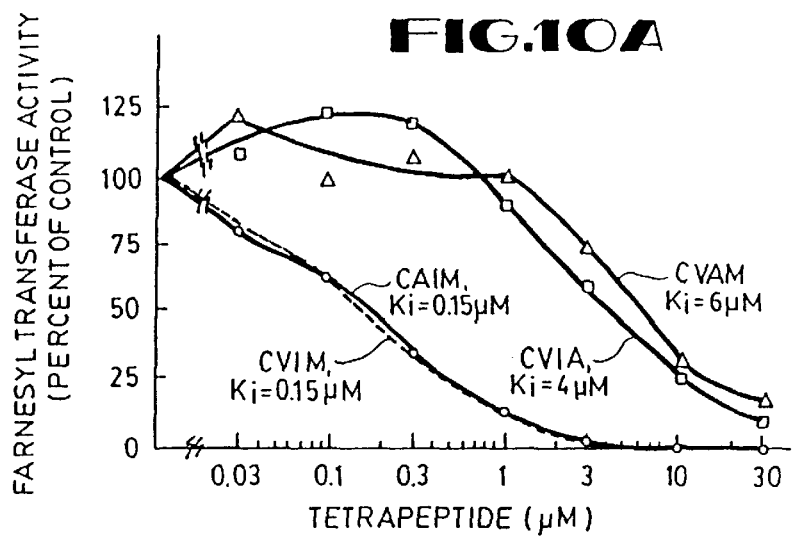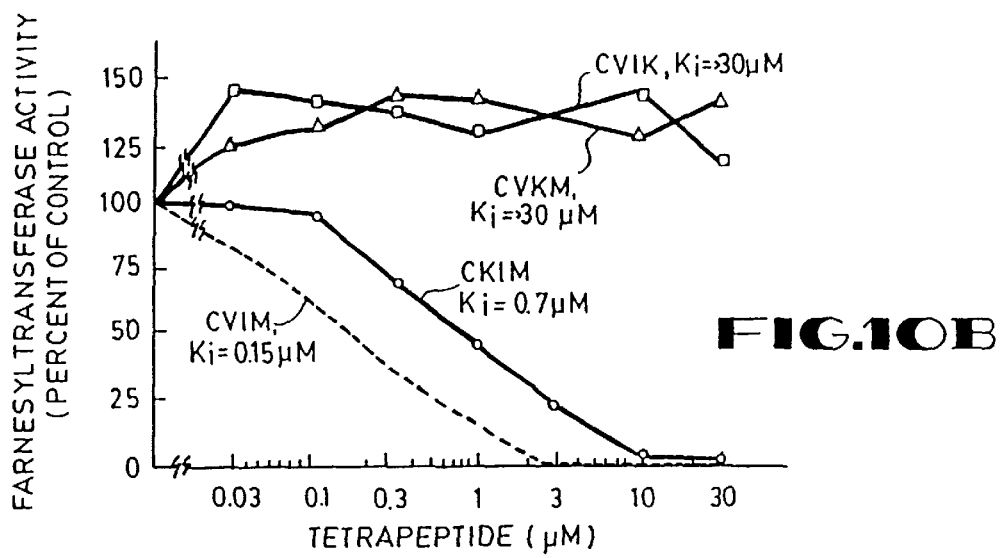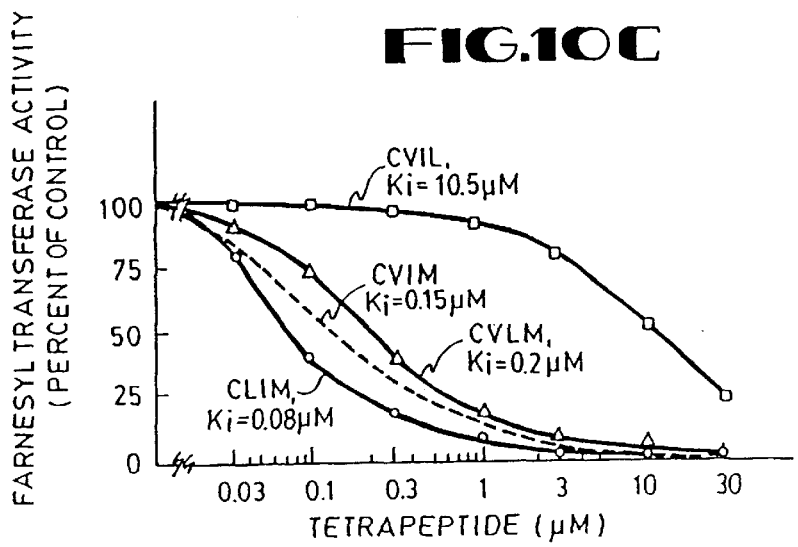

SEQUENCE LISTING

```
<160> NUMBER OF SEQ ID NOS: 52

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Arg Ala Glu Trp Ala Asp Ile Asp Pro Val Pro Gln Asn Asp Gly Pro
 1               5                  10                  15

Ser Pro Val Val Gln Ile Ile Tyr Ser
            20                  25

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Asp Ala Ile Glu Leu Asn Ala Ala Asn Tyr Thr Val Trp His Phe Arg
 1               5                  10                  15

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Asn Tyr Gln Val Trp His His Arg
 1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

His Phe Val Ile Ser Asn Thr Thr Gly Tyr Ser Asp
 1               5                  10

<210> SEQ ID NO 5
<211> LENGTH: 7
<212> TYPE: PRT
```

```
<213> ORGANISM: Artificial Sequence
<220> FEATURE:
<223> OTHER INFORMATION: Description of Artificial Sequence:  Synthetic
      Peptide

<400> SEQUENCE: 5

Val Leu Val Glu Trp Leu Lys
  1               5

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Leu Val Pro His Asn Glu Ser Ala Trp Asn Tyr Leu Lys
  1               5                  10

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Ala Tyr Cys Ala Ala Ser Val Ala Ser Leu Thr Asn Ile Ile Thr Pro
  1               5                  10                  15

Asp Leu Phe Glu
            20

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 8

Leu Gln Tyr Leu Ser Ile Ala Gln
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Leu Leu Gln Trp Val Thr Ser
  1               5

<210> SEQ ID NO 10
<211> LENGTH: 23
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10
```

Ile Gln Ala Thr Thr His Phe Leu Gln Lys Pro Val Pro Gly Phe Glu
 1               5                  10                  15

Glu Cys Glu Asp Ala Val Thr
            20

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Ile Gln Glu Val Phe Ser Ser Tyr Lys
 1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Cys Val Leu Met
 1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Cys Cys Val Gln
 1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Cys Ile Ile Cys
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Cys Ile Ile Ser
 1

<210> SEQ ID NO 16

```
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Cys Val Ile Ser
  1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17

Cys Val Leu Ser
  1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Cys Val Ile Ala
  1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Cys Val Ile Leu
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Cys Leu Ile Leu
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21
```

Cys Leu Leu Leu
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Cys Thr Val Ala
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Cys Val Ala Met
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Cys Lys Ile Met
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Cys Leu Ile Met
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Cys Val Leu Met
1

<210> SEQ ID NO 27
<211> LENGTH: 4
<212> TYPE: PRT
<213> ORGANISM: Artificial Sequence
<220> FEATURE:

<223> OTHER INFORMATION: Description of Artificial Sequence: Synthetic
      Peptide

<400> SEQUENCE: 27

Cys Phe Ile Met
 1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Cys Val Phe Met
 1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Cys Val Ile Phe
 1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Cys Glu Ile Met
 1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Cys Gly Ile Met
 1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Cys Pro Ile Met
 1

```
<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Cys Val Tyr Met
 1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34

Cys Val Thr Met
 1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

Cys Val Pro Met
 1

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

Cys Val Ser Met
 1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

Cys Val Ile Phe
 1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38
```

Cys Val Ile Val
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

Cys Val Ile Pro
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 40

Cys Val Ile Ile
1

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Lys Thr Ser Cys Val Ile Met
1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Ser Val Ile Met
1

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (6)..(9)
<223> OTHER INFORMATION: n = a, c, g and/or t/u

<400> SEQUENCE: 43
gaygcnatng arytaaacgc agccaactat acggtc                              36

<210> SEQ ID NO 44

```
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Asp Ala Ile Glu Leu Asn Ala Ala Asn Tyr Thr Val Trp His Phe Glu
  1               5                  10                  15

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (12)
<223> OTHER INFORMATION: n = a, c, g and/or t/u

<400> SEQUENCE: 45
ckraartgcc anac                                                            14

<210> SEQ ID NO 46
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (3)
<223> OTHER INFORMATION: n = a, c, g and/or t/u

<400> SEQUENCE: 46
tangagttaa acgcagccaa ctatacggtc tggcactt                                  38

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 47
gcgtactgtg cggctc                                                          16

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (3)..(12)
<223> OTHER INFORMATION: n = a, c g and/or t/u

<400> SEQUENCE: 48
gcntaytgyg cngcctcagt gcctctctca ccaac                                     35

<210> SEQ ID NO 49
<211> LENGTH: 14
```

```
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (3)..(9)
<223> OTHER INFORMATION: n = a, c, g and/or t/u

<400> SEQUENCE: 49
ggngtratna trtt                                                      14

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (33)
<223> OTHER INFORMATION: n = a, c, g and/or t/u

<400> SEQUENCE: 50
tactgtgcct cagtagcctc tctcaccaac atnatca                             37

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 51

Cys Ala Ile Leu
  1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Cys Ile Lys Ser
  1
```

METHODS OF ASSAYING FARNESYL TRANSFERASE

This is a divisional of co-pending application Ser. No. 07/937,893, filed Dec. 22, 1992, which is US nationalization of PCT application PCT/US91/02650, filed Apr. 18, 1991, which PCT application is a continuation-in-part of application Ser. No. 07/615,715, filed Nov. 20, 1990, now U.S. Pat. No. 5,141,851, which is a continuation-in-part of application Ser. No. 07/510,706, filed Apr. 18, 1990, abandoned.

This application is a continuation-in-part of copending U.S. Ser. No. 615,715, filed Nov. 20, 1990, which was a continuation-in-part of U.S. Ser. No. 510,706, filed Apr. 18, 1990.

The government may own certain rights in the present invention pursuant to NIH grant number 5-PO1-HL20948.

BACKGROUND OF THE INVENTION

1. Field of the Invention

This invention relates to the identification and characterization of an enzyme involved in expression of the cancer phenotype, as well as to the identification and selection of compounds for its inhibition. In particular aspects, the invention relates to farnesyl protein transferase enzymes which are involved in, among other things, the transfer of farnesyl groups to oncogenic ras protein.

2. Description of the Related art

In recent years, some progress has been made in the elucidation of cellular events lending to the development or progression of various types of cancers. A great amount of research has centered on identifying genes which are altered or mutated in cancer relative to normal cells. In fact, genetic research has led to the identification of a variety of gene families in which mutations can lead to the development of a wide variety of tumors. The ras gene family is a family of closely related genes that frequently contain mutations involved in many human tumors, including tumors of virtually every tumor group (see, e.g., ref. 1 for a review). In fact, altered ras genes are the most frequently identified oncogenes in human tumors (2).

The ras gene family comprises three genes, H-ras, K-ras and N-ras, which encode similar proteins with molecular weights of about 21,000 (2). These proteins, often termed. $p21^{ras}$, comprise a family of GTP-binding and hydrolyzing proteins that regulate cell growth when bound to the inner surface of the plasma membrane (3,4). Overproduction of $P21^{ras}$ proteins or mutations that abolish their GTP-ase activity lead to uncontrolled cell division (5). However, the transforming activity of ras is dependent on the localization of the protein to membranes, a property thought to be conferred by the addition of farnesyl groups (3,6).

A precedent for the covalent isoprenylation of proteins had been established about a decade ago when peptide mating factors secreted by several fungi were shown to contain a farnesyl group attached in thioether linkage to the C-terminal cysteine (7–9). Subsequent studies with the mating a-factor from *Saccharomyces cerevisiae* and farnesylated proteins from animal cells have clarified the mechanism of farnesylation. In each of these proteins the farnesylated cysteine is initially the fourth residue from the C terminus (see refs. 3, 4 and 10). Immediately after translation, in a sequence of events whose order is not yet totally established, a farnesyl group is attached to this cysteine, the protein is cleaved on the C-terminal side of this residue, and the free COOH group of the cysteine is methylated (3, 10, 11, 12). All of these reactions are required for the secretion of active a-factor in Saccharomyces (4).

DETAILED DESCRIPTION OF THE PREFERRED EMBODIMENT

Most, if not all, of the known $p21^{ras}$ proteins contain the cysteine prerequisite, which is processed by farnesylation, proteolysis and COOH-methylation, just as with the yeast mating factor (3, 4, 10, 11, 12). The farnesylated $p21^{ras}$ binds loosely to the plasma membrane, from which most of it can be released with salt (3). After binding to the membrane, some $P21^{ras}$ proteins are further modified by the addition of palmitate in thioester linkage to cysteines near the farnesylated C-terminal cysteine (3) Palmitylation renders the protein even more hydrophobic and anchors it more tightly to the plasma membrane.

However, although it appears to be clear that farnesylation is a key event in ras-related cancer development, prior to now, the nature of this event has remained obscure. Nothing has been known previously, for example, of the nature of the enzyme or enzymes which may be involved in ras tumorigenesis or required by the tumor cell to achieve farnesylation. If the mechanisms that underlie farnesylation of cancer-related proteins such as $P21^{ras}$ could be elucidated, then procedures and perhaps even pharmacologic agents could be developed in an attempt to control or inhibit expression of the oncogenic phenotype in a wide variety of cancers. It goes without saying that such discoveries would be of pioneering proportions in cancer therapy.

BRIEF DESCRIPTION OF THE DRAWINGS

The present invention addresses one or more shortcomings in the prior art through the identification and characterization of an enzyme, termed farnesyl:protein transferase, involved in the oncogenic process through the transfer of farnesyl groups to various proteins, including oncogenic ras proteins. Further, the present invention provides novel compounds, including proteins and peptides, that are capable of inhibiting the farnesyl:protein transferase enzyme.

It is therefore an object of the present invention to provide ready means for obtaining farnesyl transferase enzymes from tissues of choice using techniques which are proposed to be generally applicable to all such farnesyl protein transferases.

Figure 1A:
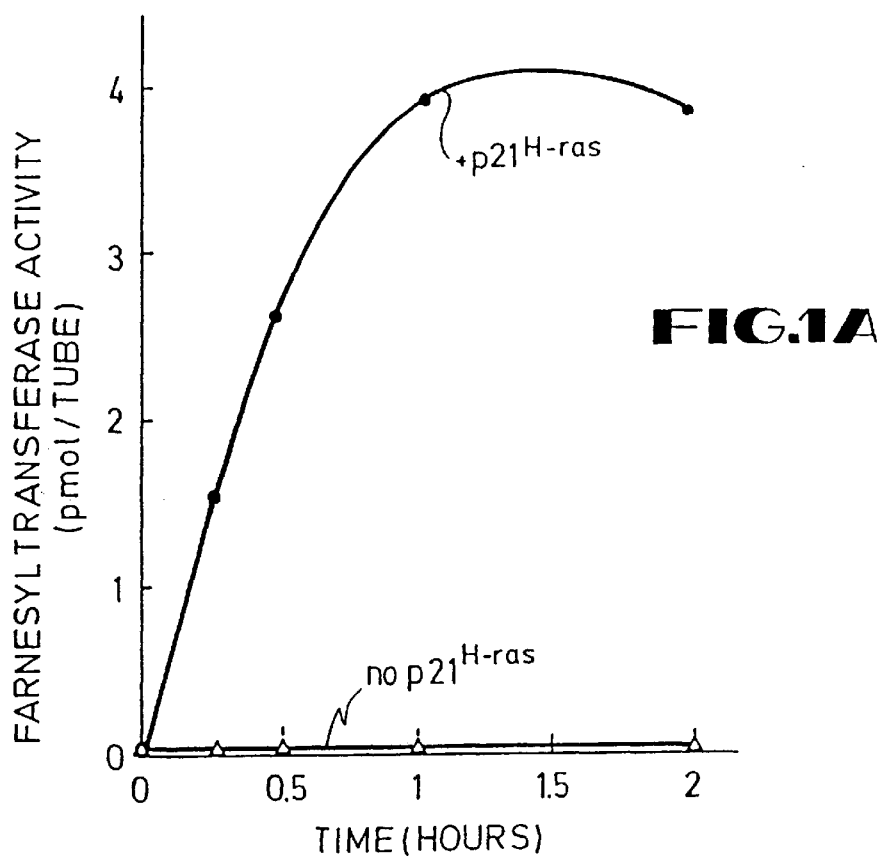

It is an additional object of the invention to provide means for obtaining these enzymes in a relatively purified form, allowing their use in predictive assays for identifying compounds having the ability to reduce the activity of or inhibit the farnesyl transferase activity, particularly in the context of $p21^{ras}$ proteins.

It is a still further object of the invention to identify classes of compounds which demonstrate farnesyl transferase inhibiting activity, along with a potential application of these compounds in the treatment of cancer, particularly ras-related cancers.

Farneayl:Protein Transferase Enzyme

Accordingly, in certain embodiments, the present invention relates to compositions which include a purified farnesyl protein transferase enzyme, characterized as follows:

a) capable of catalyzing the transfer of farnesyl to a protein or peptide having a farnesyl acceptor moiety;

b) capable of binding to an affinity chromatography medium comprised of TKCVIM coupled to a suitable matrix;

c) exhibiting a molecular weight of between about 70,000 and about 100,000 upon gel filtration chromatography; and d) having a farnesyl transferase activity that is capable of being inhibited by one of the following peptides:
  i) TKCVIM;
  ii) CVIM; or
  iii) KKSKTKCVIM.

As used. herein, the phrase "capable of catalyzing the transfer of farnesol to a protein or peptide having a farnesyl acceptor moiety," is intended to refer to the functional attributes of farnesyl transferase enzymes of the present invention, which catalyze the transfer of farnesol, typically in the form of all-trans farnesol, from all-trans farnesyl pyrophosphate to proteins which have a sequence recognized by the enzyme for attachment of the farnesyl moieties. Thus, the term "farnesyl acceptor moiety" is intended to refer to any sequence, typically a short amino acid recognition sequence, which is recognized by the enzyme and to which a farnesyl group will be attached by such an enzyme.

Farnesyl acceptor moieties have been characterized by others in various proteins as a four amino acid sequence found at the carboxy terminus of target proteins. This four amino acid sequence has been characterized as -C-A-A-X, wherein "C" is a cysteine residue, "A" refers to any aliphatic amino acid, and "X" refers to any amino acid. of course, the term "aliphatic amino acid" is well-known in the art to mean any amino acid having an aliphatic side chain, such as, for example, leucine, isoleucine, alanine, methionine, valine, etc. While the most preferred aliphatic amino acids, for the purposes of the present invention include valine and isoleucine, it is believed that virtually any aliphatic amino acids in the designated position can be recognized within the farnesyl acceptor moiety. In addition, the enzyme has been shown to recognize a peptide containing a hydroxylated amino acid (serine) in place of an aliphatic amino acid (CSIM). Of course, principal examples of proteins or peptides having a farnesyl acceptor moiety, for the purposes of the present invention, will be the $p21^{ras}$ proteins, including $p21^{H-ras}$, $p21^{K-rasA}$, $p21^{K-rasB}$ and $p21^{N-ras.}$ Thus, in light of the present disclosure, a wide variety of peptidyl sequences having a farnesyl acceptor moiety will become apparent.

As outlined above, the inventors have discovered that the farnesyl transferase enzyme is capable of binding to an affinity chromatography medium comprised of the peptide TKCVIM, coupled to a suitable matrix. This feature of the farnesyl transferase enzyme was discovered by the present inventors in developing techniques for its isolation. Surprisingly, it has been found that the coupling of a peptide such as one which includes CVIM, as does TKCVIM, to a suitable chromatography matrix allows for the purification of the protein to a significant degree, presumably through interaction and binding of the enzyme to the peptidal sequence. A basis for this interaction could be posited as due to the apparent presence of a farnesyl acceptor moiety within this peptide.

The phrase "capable of binding to an affinity chromatography medium comprised of TKCVIM coupled to a suitable matrix," is intended to refer to the ability of the protein to bind to such a medium under conditions as specified herein below. There will, of course, be conditions, such as when the pH is below 6.0, wherein the farnesyl transferase enzyme will not bind effectively to such a matrix. However, through practice of the techniques disclosed herein, one will be enabled to achieve this important objective.

There are numerous chromatography matrixes which are known in the art that can be applied to the practice of this invention. The inventors prefer to use activated CH-Sepharose 4B, to which peptides such as TKCVIM, or which incorporate the CVIM structure, can be readily attached and washed with little difficulty. However, the present invention is by no means limited to the use of CH-Sepharose 4B, and includes within its intended scope the use of any suitable matrix for performing affinity chromatography known in the art. Examples include solid matrices with covalently bound linkers, and the like, as well as matrices that contain covalently associated avidin, which can be used to bind peptides that contain biotin.

Farnesyl transferase enzymes of the present invention have typically been found to exhibit a molecular weight of between about 70,000 and about 100,000 upon gel filtration chromatography. For comparison purposes, this molecular weight was identified for farnesyl protein transferase through the use of a Superose 12 column, using a column size, sample load and parameters as described herein below.

It is quite possible, depending on the conditions employed, that different chromatographic techniques may demonstrate a farnesyl transferase protein that has an apparent molecular weight somewhat different than that identified using the preferred techniques set forth in the examples. It is intended therefore, that the molecular weight determination and range identified for farnesyl transferase in the examples which follow, are designated only with respect to the precise techniques disclosed herein.

It has been determined that the farnesyl:protein transferase can be characterized as including two subunits, each having a molecular weight of about 45 to 50 kDa, as estimated by SDS polyacrylamide gel electrophoresis (PAGE). These subunits have been designated as α and β, with the a subunit migrating slightly higher than the β subunit, which suggests that the α subunit may be slightly larger. It has also been found that the α and β subunits have different amino acid sequences as determined by sequence analysis of tryptic digests prepared from the two purified proteins, and appear to be produced by separate genes. The peptide sequences obtained from the two proteins from rat brain are as follows:

TABLE I

Farnesyl: Protein Transferase Peptide Sequences

α subunit:

1) R A E W A D I D P V P Q N D G P S P V V Q I I Y S   SEQ ID NO:1
2) D A I E L N A A N Y T V W H F R                     SEQ ID NO:2
3) N Y Q V W H H R                                     SEQ ID NO:3
4) H F V I S N T T G Y S D                             SEQ ID NO:4
5) V L V E W L K                                       SEQ ID NO:5
6) L V P H N E S A W N Y L K                           SEQ ID NO:6

TABLE I-continued

Farnesyl: Protein Transferase Peptide Sequences

β subunit:

```
 7) A Y C A A S V A S L T N I I T P D L F E        SEQ ID NO:7
 8) L Q Y L S I A Q                                SEQ ID NO:8
 9) L L Q W V T S                                  SEQ ID NO:9
10) I Q A T T H F L Q K P V P G F E E C⁷E D A V T  SEQ ID NO:10
11) I Q E V F S S Y K                              SEQ ID NO:11
```

The inventors have found that the holoenzyme forms a stable complex with [$^3$H]farnesyl pyrophosphate (FPP) that can be isolated by gel electrophoresis. The [$^3$H]FFP is not covalently bound to the enzyme, and is released unaltered when the enzyme is denatured. When incubated with an acceptor such as p21$^{H\text{-}ras}$, the complex transfers [$^3$H]farnesyl from the bound [$^3$H]FFP to the ras protein. Furthermore, crosslinking studies have shown that p21$^{H\text{-}ras}$ binds to the β subunit, raising the possiblity that the [$^3$H]FFP binds to the α subunit. If this is the case, it would invoke a reaction mechanism in which the α subunit act as a prenyl pyrophosphate carrier that delivers FPP to p21$^{H\text{-}ras}$, which is bound to the β subunit. Interestingly, the inventors have recenlty discovered that the a subunit is shared with another prenyltransferase, geranylgeranyltransferase, that attaches 20-carbon geranylgeranyl to ras-related proteins.

An additional property discovered for farnesyl transferase enzymes is that they can be inhibited by peptides or proteins, particularly short peptides, which include certain structural features, related in some degree to the farnesyl acceptor moiety discussed above. As used herein, the word "inhibited" refers to any degree of inhibition and is not limited for these purposes to only total inhibition. Thus, any degree of partial inhibition or relative reduction in farnesyl transferase activity is intended to be included within the scope of the term "inhibited." Inhibition in this context includes the phenomenon by which a chemical constitutes an alternate substrate for the enzyme, and is therefore farnesylated in preference to the ras protein, as well as inhibition where the compound does not act as an alternate substrate for the enzyme.

Preparation of Farnesyl:Protein Transferase

The present invention is also concerned with particular techniques for the identification and isolation of farnesyl transferase enzymes. An important feature of the purification scheme disclosed herein involves the use of short peptide sequences which the inventors have discovered will bind the enzyme, allowing their attachment to chromatography matrices, such matrices may in turn, be used in connection with affinity chromatography to purify the enzyme to a relative degree. Thus, the present invention is concerned with a method of preparing a farnesyl transferase enzyme which includes the steps of:

(a) preparing a cellular extract which includes the enzyme;

(b) subjecting the extract to affinity chromatography on an affinity chromatography medium to bind the enzyme thereto, the medium comprised of a farnesyl transferase binding peptide coupled to a suitable matrix;

(c) washing the medium to remove impurities; and (d) eluting the enzyme from the washed medium.

Thus, the first step of the purification protocol involves simply preparing a cellular extract which includes the enzyme. The inventors have discovered that the enzyme is soluble in buffers such as low-salt buffers, and it is proposed that virtually any buffer of this type can be employed for initial extraction of the protein from a tissue of choice. The inventors prefer a 50 mM Tris-chloride, pH 7.5, buffer which includes divalent chelator (e.g., 1 mM EDTA, 1 mM EGTA), as well as protease inhibitors such as PMSF and/or leupeptin. Of course, those of skill in the art will recognize that a variety of other types of tissue extractants may be employed where desired, so long as the enzyme is extractable in such a buffer and its subsequent activity is not adversely affected to a significant degree.

The type of tissue from which one will seek to obtain the farnesyl transferase enzyme is not believed to be of crucial importance. It is, in fact, believed that farnesyl transferase enzyme is a component of virtually all living cells. Therefore, the tissue of choice will typically be that which is most readily available to the practitioner. In that farnesyl transferase action appears to proceed similarly in most systems studied, including, yeast, cultured hamster cells and rat brain, it is believed that this enzyme will exhibit similar qualities, regardless of its source of isolation.

In preferred embodiments, the inventors have isolated the enzyme from rat brains in that this source is readily available. However, numerous other sources are contemplated to be directly applicable for isolation of the enzyme, including liver, yeast, reticulocytes, and even human placenta. Those of skill in the art, in light of the present disclosure, should appreciate that the techniques disclosed herein will be generally applicable to all such farnesyl transferases.

After the cell extract is prepared the enzyme is preferably subjected to two partial purification steps prior to affinity chromatography. These steps comprise preliminary treatment with 30% saturated ammonium sulfate which removes certain contaminants by precipitation. This is followed by treatment with 50% saturated ammonium sulfate, which precipitates the farnesyl transferase. The pelleted enzyme is then dissolved, preferably in a solution of 20 mM Tris-chloride (pH 7.5) containing 1 mM DTT and 20 µM ZnCl$_2$. After dialysis against the same buffer the enzyme solution is applied to an ion exchange column containing an ion exchange resin such as Mono Q. After washing of the column, the enzyme is eluted with a gradient of 0.25–1.0 M NaCl in the same buffer. The enzyme activity in each fraction is assayed as described below, and the fractions containing active enzyme are pooled and applied to the affinity column described below.

It is, of course, recognized that the preliminary purification steps described above are preferred laboratory procedures that might readily be replaced with other procedures of equivalent effect such as ion exchange chromatography on other resins or gel filtration chromatography. Indeed, it is possible that these steps could even be omitted and the crude cell extract might be carried directly to affinity chromatography.

After the preliminary purification steps, the extract may be subjected to affinity chromatography on an affinity chromatography medium which includes a farnesyl transferase binding peptide coupled to a suitable matrix. Typically, preferred farnesyl transferase binding peptides will comprise a peptide of at least 4 amino acids in length and will include a carboxy terminal sequence of -C-A-A-X, wherein:

C=cysteine;
A=an aliphatic or hydroxy amino acid; and
X=any amino acid.

Preferred binding peptides of the present invention which fall within the above general formula include structures such as -C-V-I-M, -C-S-I-M and -C-A-I-M, all of which structures are found to naturally occur in proteins which are believed to be acted upon by farnesyl protein transferases in nature. Particularly preferred are relatively short peptides, such as on the order of about 4 to 10 amino acids in length which incorporate one of the foregoing binding sequences. Of particular preference is the peptide T-K-C-V-I-M which is routinely employed by the inventors in the isolation of farnesyl protein transferase.

The next step in the overall general purification scheme involves simply washing the medium to remove impurities. That is, after subjecting the extract to affinity chromatography on the affinity matrix, one will desire to wash the matrix in a manner that will remove the impurities while leaving the farnesyl transferase enzyme relatively intact on the medium. A variety of techniques are known in the art for washing matrices such as the one employed herein, and all such washing techniques are intended to be included within the scope of this invention. Of course, for washing purposes, one will not desire to employ buffers that will release or otherwise alter or denature the enzyme. Thus, one will typically want to employ buffers which contain non-denaturing detergents such as octylglucoside buffers, but will want to avoid buffers containing, e.g., chaotropic reagents which serve to denature proteins, as well as buffers of low pH (e.g., less than 7), or of high ionic strength (e.g., greater than 1.0M), as these buffers tend to elute the bound enzyme from the affinity matrix.

After the matrix-bound enzyme has been sufficiently washed, for example in a medium-ionic strength buffer at essentially neutral pH, the specifically bound material can be eluted from the column by using a similar buffer but of reduced pH (for example, a pH of between about 4 and 5.5). At this pH, the enzyme will typically be found to elute from the preferred affinity matrices disclosed in more detail hereinbelow.

While it is believed that advantages in accordance with the invention can be realized simply through affinity chromatography techniques, additional benefits will be achieved through the application of additional purification techniques, such as gel filtration techniques. For example, the inventors have discovered that Sephacryl S-200 high resolution gel columns can be employed with significant benefit in terms of protein purification. However, the present disclosure is by no means limited to the use of Sephacryl S-200, and it is believed that virtually any type of gel filtration arrangement can be employed with some degree of benefit. For example, one may wish to use techniques such as gel filtration, employing media such as Superose, Agarose, or even Sephadex.

Through the application of various of the foregoing approaches, the inventors have successfully achieved farnesyl transferase enzyme compositions of relatively high specific activity, measured in terms of ability to transfer farnesol from farnesyl pyrophosphate. For the purposes of the present invention, one unit of activity is defined as the amount of enzyme that transfers 1 pmol of farnesol from farnesyl pyrophosphate (FPP) into acid-precipitable $p21^{H\text{-}ras}$ per hour under the conditions set forth in the Examples. Thus, in preferred embodiments the present invention is concerned with compositions of farnesyl transferase which include a specific activity of between about 5 and about 10 units/mg of protein. In more preferred embodiments, the present invention is concerned with compositions which exhibit a farnesyl transferase specific activity of between about 500 and about 600,000 units/mg of protein. Thus, in terms of the unit definition set forth above, the inventors have been able to achieve compositions having a specific activity of up to about 600,000 units/mg using techniques disclosed herein.

Of principal importance to the present invention is the discovery that proteins or peptides which incorporate a farnesyl acceptor sequence, such as one of the farnesyl acceptor sequences discussed above, function as inhibitors of farnesyl:protein transferase, and therefore may serve as a basis for anticancer therapy. In particular, it has been found that farnesyl acceptor peptides can successfully function both as false substrates that serve to inhibit the farnesylation of natural substrates such as $p21^{ras}$, and as direct inhibitors which are not themselves farnesylated. Compounds falling into the latter category are particularly important in that these compounds are "pure" inhibitors that are not consumed by the inhibition reaction and can continue to function as inhibitors. Both types of compounds constitute an extremely important aspect of the invention in that they provide a means for blocking farnesylation of $p21^{ras}$ proteins, for example, in an affected cell system.

Inhibitors or Farnesyl:Protein Transferase

The farnesyl transferase inhibitor embodiments of the present invention concern in a broad sense a peptide or protein other than $p21^{ras}$ proteins, lamin a or lamin b, or yeast mating factor a, which peptide or protein includes a farnesyl acceptor sequence within its structure and is further capable of inhibiting the farnesylation of $p21^{ras}$ by farnesyl transferase.

In preferred embodiments, the farnesyl transferase inhibitor of the present invention will include a farnesyl acceptor or inhibitory amino acid sequence having the amino acids -C-A-A-X, wherein:

C=cysteine;
A=any aliphatic, aromatic or hydroxy amino acid; and
X=any amino acid.

Typically, the farnesyl acceptor or inhibitory amino acid sequence will be positioned at the carboxy terminus of the protein or peptide such that the cysteine residue is in the fourth position from the carboxy terminus.

In preferred embodiments, the inhibitor will be a relatively short peptide such as a peptide from about 4 to about 10 amino acids in length. To date, the most preferred inhibitor tested is a tetrapeptide which incorporates the -C-A-A-X recognition structure. It is possible that even shorter peptides will ultimately be preferred for practice of the invention in that the shorter the peptide, the greater the uptake by such peptide by biological systems, and the reduced likelihood that such a peptide will be destroyed or otherwise rendered biologically ineffective prior to effecting inhibition. However, numerous suitable inhibitory peptides have been prepared and tested by the present inventors, and shown to inhibit enzymatic activities virtually completely, at reasonable concentrations, e.g., between about 1 and 3 $\mu$M (with 50% inhibitions on the order of 0.1 to 0.5 $\mu$M).

While, broadly speaking, it is believed that compounds exhibiting an $IC_{50}$ of between about 0.01 $\mu$M and 10 $\mu$M will have some utility as farnesyl transferase inhibitors, the more preferred compounds will exhibit an IC$_{50}$ of between 0.01 μM and 1 μM. The most preferred compounds will generally have an IC$_{50}$ of between about 0.01 μM and 0.3 μM.

Exemplary peptides which have been prepared, tested and shown to inhibit farnesyl transferase at an IC$_{50}$ of between 0.01 and 10 μM include CVIM; KKSKTKCVIM; TKCVIM; RASNRSCAIM; TQSPQNCSIM; CIIM;, CVVM; CVLS; CVLS; CVLM; CAIM; CVLM(SEQ ID NO:12); CCVQ (SEQ ID NO:13); CIIC(SEQ ID NO:14); CIIS(SEQ ID NO15); CVIS(SEQ ID NO:16); CVLS(SEQ ID NO:17); CVIA(SEQ ID NO:18); CVIL(SEQ ID NO:19); CLIL(SEQ ID NO:20); CLLL(SEQ ID NO:21); CTVA(SEQ ID NO:22); CVAM(SEQ ID NO:23); CKIM(SEQ ID NO:24); CLIM(SEQ ID NO:25); CVLM(SEQ ID NO:26); CFIM (SEQ ID NO:27); CVFM(SEQ ID NO:28); CVIF(SEQ ID NO:29); CEIM(SEQ ID NO:30); CGIM(SEQ ID NO:31); CPIM(SEQ ID NO:32); CVYM(SEQ ID NO:33); CVTM (SEQ ID NO:34); CVPM(SEQ ID NO:35); CVSM(SEQ ID NO:36); CVIF(SEQ ID NO:37); CVIV(SEQ ID NO:38); CVIP(SEQ ID NO:39); CVII(SEQ ID NO:40).

A variety of peptides have been synthesized and tested such that now the inventors can point out peptide sequencing having particularly high inhibitory activity, i.e., wherein relatively lower concentrations of the peptides will exhibit an equivalent inhibitory activity (IC$_{50}$). Interestingly, it has been found that slight changes in the sequence of the acceptor site can result in loss of inhibitory activity. Thus, when TKCVIM is changed to TKVCIM, the inhibitory activity of the peptide is reversed. Similarly, when a glycine is substituted for one of the aliphatic amino acids in CAAX, a decrease in inhibitory activity is observed. However, it is proposed that as long as the general formula as discussed above is observed, one will achieve a structure that is inhibitory to farnesyl transferase.

A particularly important discovery is the finding that the incorporation of an aromatic residue such as phenylalanine, tyrosine or tryptophan into the third position of the CAAX sequence will result in a "pure" inhibitor. As used herein, a "pure" farnesyl:protein transferase inhibitor is intended to refer to one which does not in itself act as a substrate for farnesylation by the enzyme. This is particularly important in that the inhibitor is not consumed by the inhibition process, leaving the inhibitor to continue its inhibitory function unabated. Exemplary compounds which have been tested and found to act as pure inhibitors include CVIF (SEQ ID NO:29), CVFM (SEQ ID NO:28), and CVYM (SEQ ID NO:33). Pure inhibitors will therefore incorporate an inhibitory amino acid sequence rather than an acceptor sequence, with the inhibitory sequence characterized generally as having an aromatic moiety associated with the penultimate carboxy terminal amino acid, whether it be an aromatic amino acid or another amino acid which has been modified to incorporate an aromatic structure.

Importantly, the pure inhibitor CVFM is the best inhibitor identified to date by the inventors. It should be noted that the related peptide, CFVM (SEQ ID NO:28) is not a "pure" inhibitor; its inhibitory activity is due to its action as a substrate for farnesylation.

The potency of CVFM peptides as inhibitors of the enzyme may be enhanced by attaching substituents such as fluoro, chloro or nitro derivatives to the phenyl ring. An example is parachlorophenylalanine, which has been tested and found to have "pure" inhibitory activity. It may also be possible to substitute more complex hydrophobic substances for the phenyl group of phenylalanine. These would include naphthyl ring systems.

The present inventors propose that additional improvements can be made in pharmaceutical embodiments of the inhibitor by including within their structure moieties which will improve their hydrophobicity, which it is proposed will improve the uptake of peptidyl structures by cells. Thus, in certain embodiments, it is proposed to add fatty acid or polyisoprenoid side chains to the inhibitor which, it is believed, will improve their lipophilic nature and enhance their cellular uptake.

Other possible structural modifications include the addition of benzyl, phenyl or acyl groups to the amino acid structures, preferably at a position sufficiently removed from the farnesyl acceptor site, such as at the amino terminus of the peptides. It is proposed that such structures will serve to improve lypophilicity. In this regard, the inventors have found that N-acetylated and N-octylated peptides such as modified CVIM retain there much of their inhibitory activity, whereas S-acetoamidated CVIM appears to lose much of its inhibitory activity.

The invention also contemplates that modifications can be made in the structure of inhibitory proteins or peptides to increase their stability within the body, such as modifications that will reduce or eliminate their susceptibility to degradation, e.g., by proteases. For example, the inventors contemplate that useful structural modifications will include the use of amino acids which are less likely to be recognized and cleaved. by proteases, such as the incorporation of D-amino acids, or amino acids not normally found in proteins such as ornithine or taurine. Other possible modifications include the cyclization of the peptide, derivatization of the NH groups of the peptide bonds with acyl groups, etc.

Assays for Farnesyl:Protein Transferase

In still further embodiments, the invention concerns a method for assaying farnesyl transferase activity in a composition. This is an important aspect of the invention in that such an assay system provides one with not only the ability to follow isolation and purification of the enzyme, but it also forms the basis for developing a screening assay for candidate inhibitors of the enzyme, discussed in more detail below. The assay method generally includes simply determining the ability of a composition suspected of having farnesyl transferase activity to catalyze the transfer of farnesol to an acceptor protein or peptide. As noted above, a farnesyl acceptor protein or peptide is generally defined as a protein or peptide which will act as a substrate for farnesyl transferase and which includes a recognition site such as -C-A-A-X, as defined above.

Typically, the assay protocol is carried out using farnesyl pyrophosphate as the farnesol donor in the reaction. Thus, one will find particular benefit in constructing an assay wherein a label is present on the farnesyl moiety of farnesyl pyrophosphate, in that one can measure the appearance of such a label, for example, a radioactive label, in the farnesyl acceptor protein or peptide.

As with the characterization of the enzyme discussed above, the farnesyl acceptor sequence which are employed in connection with the assay can be generally defined by -C-A-A-X, with preferred embodiments including sequences such as -C-V-I-M, -C-S-I-M, -C-A-I-M, etc., all of which have been found to serve as useful enzyme substrates. It is believed that most proteins or peptides that include a carboxy terminal sequence of -C-A-A-X can be successfully employed in farnesyl protein transferase assays. For use in the assay a preferred farnesyl acceptor protein or peptide will be simply a p21$^{ras}$ protein. This is particularly true where one seeks to identify inhibitor substances, as discussed in more detail below, which function either as "false acceptors" in that they divert farnesylation away from natural substrates by acting as substrates in and or themselves, or as "pure" inhibitors which are not in themselves farnesylated. The advantage of employing a natural substrate such as p21$^{ras}$ is several fold, but includes the ability to separate the natural substrate from the false substrate to analyze the relative degrees of farnesylation.

However, for the purposes of simply assaying enzyme specific activity, e.g., assays which do not necessarily involve differential labeling or inhibition studies, one can readily employ short peptides as a farnesyl acceptor in such protocols, such as peptides from about 4 to about 10 amino acids in length which incorporate the recognition signal at their carboxy terminus. Exemplary farnesyl acceptor protein or peptides include but are not limited to CVIM; KKSKT-KCVIM; TKCVIM; RASNRSCAIM; TQSPQNCSIM; CIIM; CVVM; and CVLS.

Assays for Candidate Substances

In still further embodiments, the present invention concerns a method for identifying new farnesyl transferase inhibitory compounds, which may be termed as "candidate substances." It is contemplated that this screening technique will prove useful in the general identification of any compound that will serve the purpose of inhibiting farnesyl transferase. It is further contemplated that useful compounds in this regard will in no way be limited to proteinaceous or peptidyl compounds. In fact, it may prove to be the case that the most useful pharmacologic compounds for identification through application of the screening assay will be non-peptidyl in nature and, e.g., which will be recognized and bound by the enzyme, and serve to inactivate the enzyme through a tight binding or other chemical interaction.

Thus, in these embodiments, the present invention is directed to a method for determining the ability of a candidate substance to inhibit a farnesyl transferase enzyme, the method including generally the steps of:

(a) obtaining an enzyme composition comprising a farnesyl transferase enzyme that is capable of transferring a farnesyl moiety to a farnesyl acceptor substance;

(b) admixing a candidate substance with the enzyme composition; and (c) determining the ability of the farnesyl transferase enzyme to transfer a farnesyl moiety to a farnesyl acceptor substrate in the presence of the candidate substance.

An important aspect of the candidate substance screening assay hereof is the ability to prepare a farnesyl transferase enzyme composition in a relative purified form, for example, in a manner as discussed above. This is an important aspect of the candidate substance screening assay in that without at least a relatively purified preparation, one will not be able to assay specifically for enzyme inhibition, as opposed to the effects of the inhibition upon other substances in the extract which then might affect the enzyme. In any event, the successful isolation of the farnesyl transferase enzyme now allows for the first time the ability to identify new compounds which can be used for inhibiting this cancer-related enzyme.

The candidate screening assay is quite simple to set up and perform, and is related in many ways to the assay discussed above for determining enzyme activity. Thus, after obtaining a relatively purified preparation of the enzyme, one will desire to simply admix a candidate substance with the enzyme preparation, preferably under conditions which would allow the enzyme to perform its farnesyl transferase function but for inclusion of a inhibitory substance. Thus, for example, one will typically desire to include within the admixture an amount of a known farnesyl acceptor substrate such as a p21$^{ras}$ protein. In this fashion, one can measure the ability of the candidate substance to reduce farnesylation of the farnesyl acceptor substrate relatively in the presence of the candidate substance.

Accordingly, one will desire to measure or otherwise determine the activity of the relatively purified enzyme in the absence of the added candidate substance relative to the activity in the presence of the candidate substance in order to assess the relative inhibitory capability of the candidate substance.

Methods of Inhibiting Parnesyl:Protein Transferase

In still further embodiments, the present invention is concerned with a method of inhibiting a farnesyl transferase enzyme which includes subjecting the enzyme to an effective concentration of a farnesyl transferase inhibitor such as one of the family of peptidyl compounds discussed above, or with a candidate substance identified in accordance with the candidate screening assay embodiments. This is, of course, an important aspect of the invention in that it is believed that by inhibiting the farnesyl transferase enzyme, one will be enabled to treat various aspects of cancers, such as ras-related cancers. It is believed that the use of such inhibitors to block the attachment of farnesyl groups to ras proteins in malignant cells of patients suffering with cancer or pre-cancerous states will serve to treat or palliate the cancer, and may be useful by themselves or in conjunction with other cancer therapies, including chemotherapy, resection, radiation therapy, and the like.

Genes Encoding Farnesyl:Protein Transferase Enzyme

In still further embodiments, the invention relates to the preparation of farnesyl:protein transferase through the application of recombinant DNA technology. The inventors have recently determined the feasibility of isolating genes encoding one or both of the farnesyl:protein transferase subunits. It is proposed that such recombinant genes may be employed for a variety of applications, including, for example, the recombinant production of the subunits themselves or proteins or peptides whose structure is derived from that of the subunits, in the preparation of nucleic acid probes or primers, which can, for example, be used in the identification of related gene sequences or studying the expression of the subunit(s), and the like.

It is proposed that the recombinant cloning of the genes encoding the respective a and P subunits may be achieved most readily through the use of the peptide sequence information set forth above. The direct manner in which to proceed with such cloning is through the preparation of a recombinant clone bank, preferably cDNA clone bank using poly A$^+$ RNA from a desired cell source (although it is believed that where desired, one could employ a genomic bank). In that the enzyme appears to be fairly ubiquitous in nature, it is believed that virtually any eukaryotic cell source may be employed for the initial preparation of RNA. One may mention by way of example, yeast, mammalian, plant, eukaryotic parasites and even viral-infected types of cells as the source of starting poly A$^+$ RNA.

Since the protein was initially purified from a mammalian source (rat), one may find particular advantage in employing a mammalian cell source, such as a rat or human cell line, as an RNA source. It may, however, be advantageous to first test the cell to be employed to ensure that relatively high levels of the enzyme are being produced by the selected cell line. Rat brain, PC12 (a rat adrenal tumor cell line) and KNRK (a newborn rat kindney cell line) cells are presently the most preferred by the inventors in that they very high levels of endogenous farnesyl:protein transferase activity. The inventors have proceeded in initial studies employing the foregoing cell types as sources of RNA.

It is believed that the type of CDNA clone bank is not particularly crucial. However, one will likely find particular benefit through the preparation and use of a phage-based bank, such as λgt10 or λgt11, preferably using a particle packaging system. Phage-based cDNA banks are preferred because of the large numbers of recombinants that may be prepared and screened will relative ease. The manner in which the cDNA itself is prepared is not believed to be particularly crucial. However, the inventors believe that it may be beneficial to employ the both oligo dT as well as randomly primed cDNA in that the size of the mRNA encoding the farnesyl:protein transferase may be large and thus difficult to reverse transcribe in its entirety.

Once a clone bank has been prepared, it may be screened in a number of fashions. For example, one could employ the subunit peptide sequences set forth above for the preparation of nucleotide probes which may be employed directly to screen the bank by hybridization screening. However, a more preferred approach is to use the peptide sequences in the preparation of primers which may be used in PCR-based reactions to amplify and then sequence portions of the selected subunit gene, to thereby confirm the actual underlying DNA sequence, and to prepare longer and more specific probes for screening. These primers may also be employed for the preparation of cDNA clone banks which are enriched for 3' and/or 5' sequences. This may be important, e.g., where less than a full length clone is obtained through the initially prepared bank.

Once a positive clone or clones have been obtained, and engineered to ensure a full length sequence (if needed and where desired), one may proceed to prepare an expression system for the recombinant preparation of one or both subunits. It is believed that virtually any expression system may be employed for preparing one or both subunits. For example, it is envisioned that even bacterial expression systems may be employed, e.g., where one envisions using the subunit for its immunologic rather than biologic properties. Of course, where a biologically active enzyme is needed, one will prefer to employ a eukaryotic expression system employing eukaryotic cells, most preferably cotransformed with DNA encoding both subunits.

It is believed that virtually any eukaryotic expression system may be employed as desired. A preferred system for expression of farnesyl:protein transferase DNA is a cytomegalo virus promoter-based expression vector in simian COS cells or human embryonic kidney 293 cells, although other systems, including but not limited to baculovirus-based, glutamine synthase-based or dihydrofolate reductase-based systems may prove to be particularly useful. It is believed that once a full length recombinant gene has been obtained, whether it be cDNA based or genomic, then the engineering of such a gene for expression in a prokaryotic or eukaryotic system may be performed by techniques generally known to those of skill in recombinant expression.

Figure 1B:
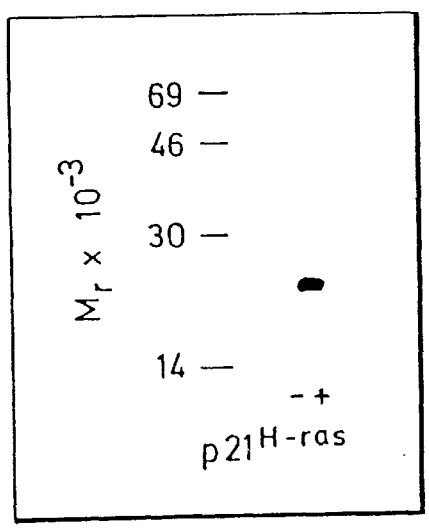

The invention is described in part by reference to the following figures:

FIG. 1. Transfer of Farnesol from [$^3$H]FPP to p21$^{H\text{-}ras}$ by Partially Purified Rat Brain Farnesyl:Protein Transferase. Each standard assay mixture contained 10 pmoles of [$^3$H] FPP and 3.5 μg of partially purified farnesyl transferase in the absence (▲) or presence (●) of 40 μM p21$^{H\text{-}ras}$. Duplicate samples were incubated for the indicated time at 37° C., and TCA-precipitable radioactivity was measured as described in the Examples. The inset shows the migration on a 12% SDS polyacrylamide gel of an aliquot from a reaction carried out for 1 h in the absence or presence of p21$^{H\text{-}ras}$. The gel was treated with Entensify solution (DuPont), dried, and exposed to XAR film for 2 days at −70° C.

FIG. 2. Substrate Saturation Curves for Farnesyl:Protein Transferase. Panel A, each standard reaction mixture contained 1.8 μg of partially purified farnesyl transferase, 40 μg p21$^{H\text{-}ras}$, [$^3$H]FPP (250,000 dpm); and varying amounts of unlabeled FPP to give the indicated final concentration of [$^3$H]FPP. Panel B, each standard reaction mixture contained 3.2 μg partially purified farnesyl transferase, 10 pmol [$^3$H] FPP, and the indicated concentration of p21$^{H\text{-}ras}$ that had been incubated with 50 μM of the indicated nucleotide for 45 min at 30° C. and then passed through a G-50 Sephadex gel filtration column at room temperature in buffer containing 10 mM Tris-chloride (pH 7.7), 1 mM EDTA, 1 mM DTT, and 3 mM MgCl$_2$. For both panels, assays were carried out in duplicate for 1 h at 37° C., and TCA-precipitable radioactivity was measured as described in the Example.

FIG. 3. Divalent Cation Requirement for Farnesyl:Protein Transferase. Each standard reaction mixture contained 10 pmol [$^3$H]FPP, 2.5 μg of partially purified farnesyl transferase, 40 μM p21$^{H\text{-}ras}$, 0.15 mM EDTA, and the indicated concentrations of either ZnCl$_2$ (●) or MgCl$_2$ (▲). Incubations were carried out in duplicate for 1 h at 37° C., and TCA-precipitable radioactivity was measured as described in the Examples.

Figure 4A:
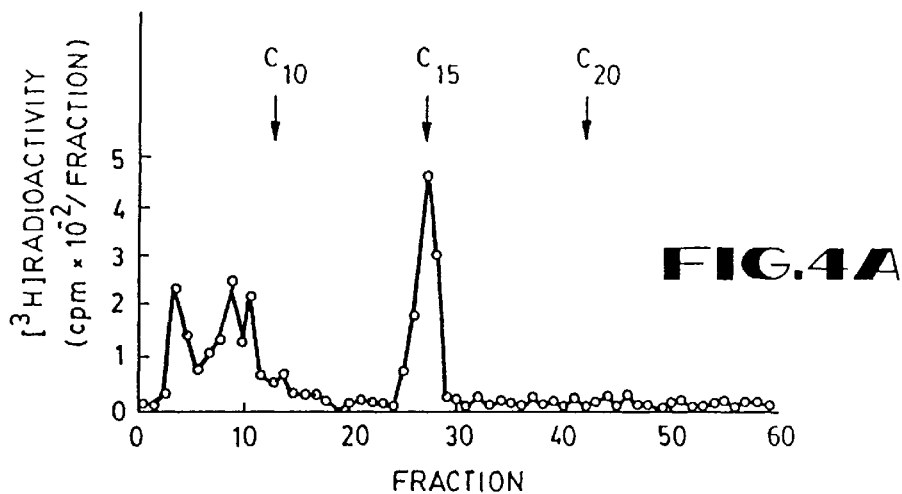
Figure 4B:
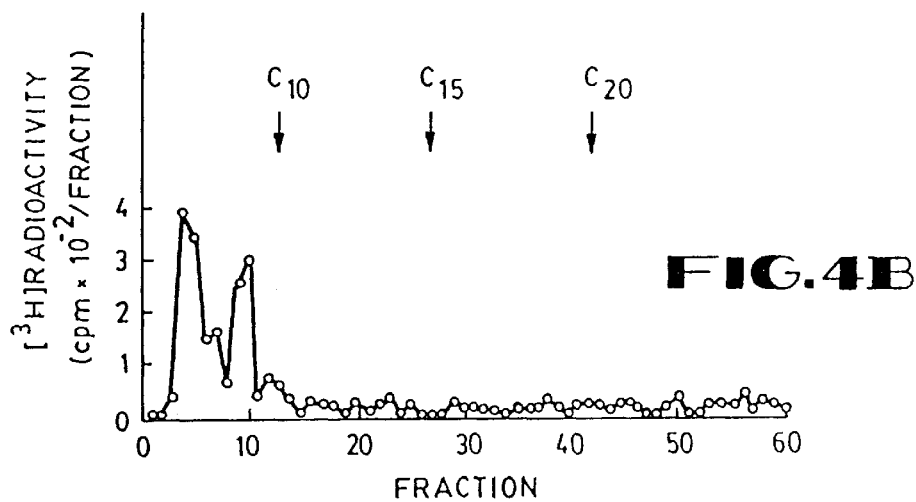

FIG. 4. Identification of [$^3$H]FPP-derived Radioactive Material Transferred to p21$^{H\text{-}ras}$. Panel A, an aliquot from a standard reaction mixture was subjected to cleavage with methyl iodide as described in the Examples. Panel B, another aliquot was treated identically except methyl iodide was omitted. After cleavage, the extracted material was dried under nitrogen, resuspended in 0.4 ml of 50% (v/v) acetonitrile containing 25 mM phosphoric acid and 6 nmoles of each isoprenoid standard as indicated. The mixture was subjected to reverse phase HPLC (C18, Phenomex) as described by Casey, et al. (6) except that an additional 10-min wash with 100% acetonitrile/phosphoric acid was used. The isoprenoid standards were identified by absorbance at 205 nm: C$_{10}$, all-trans geraniol; C$_{15}$, all-trans farnesol; C$_{20}$, all-trans geranylgeraniol.

Figure 5:
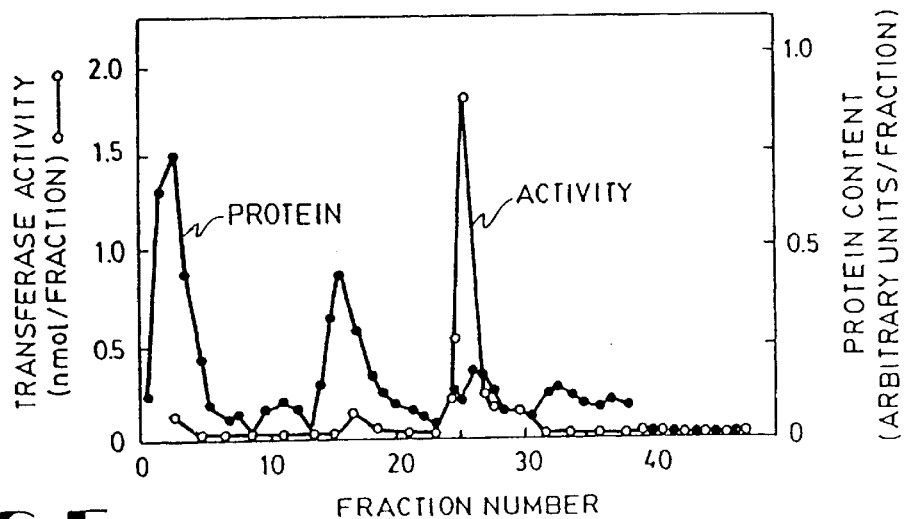

FIG. 5. Chromatography of Farnesyl:Protein Transferase on a Mono Q Column. The 30–50% ammonium sulfate fraction from rat brain (200 mg) was applied to a Mono Q column (10×1-cm) equilibrated in 50 mM Tris-chloride (pH 7.5) containing 1 mM DTT, 20 μM ZnCl$_2$, and 0.05 M NaCl. The column was washed with 24 ml of the same buffer containing 0.05 M NaCl, followed by a 24-ml linear gradient from 0.05 to 0.25 M NaCl, followed by a second wash with 24 ml of the same buffer containing 0.25 M NaCl. The enzyme was then eluted with a 112-ml linear gradient of the same buffer containing 0.25–1.0 M NaCl at a flow rate of 1 ml/min. Fractions of 4 ml were collected. An aliquot of each fraction (2 μl) was assayed for farnesyl:protein transferase activity by the standard method (○). The protein content of each fraction (●) was estimated from the absorbance at 280 mM.

Figure 6A:
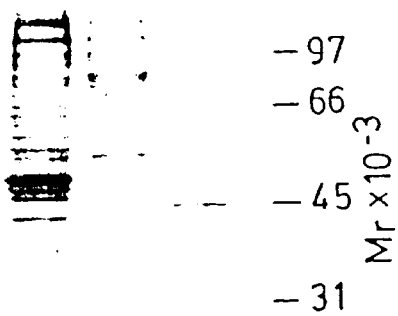

FIG. 6A. SDS Polyacrylamide Gel Electrophoresis of Farnesyl:Protein Transferase at Various Stages of Purification. 10 μg of the 30–50% ammonium sulfate fraction (lane 1), 3 μg of the Mono Q fraction (lane 2), and approximately 90 ng of the peptide affinity-column fraction (lane 3) were subjected to SDS-10% polyacrylamide gel electrophoresis, and the protein bands were detected with a silver stain. The farnesyl:protein transferase activity in each sample loaded onto the gel was approximately 0.1, 0.8, and 54 units/lane for lanes 1, 2, and 3, respectively. The molecular weights for marker protein standards are indicated. Conditions of electrophoresis: 10% mini gel run at 30 mA for 1 h.

Figure 6B:
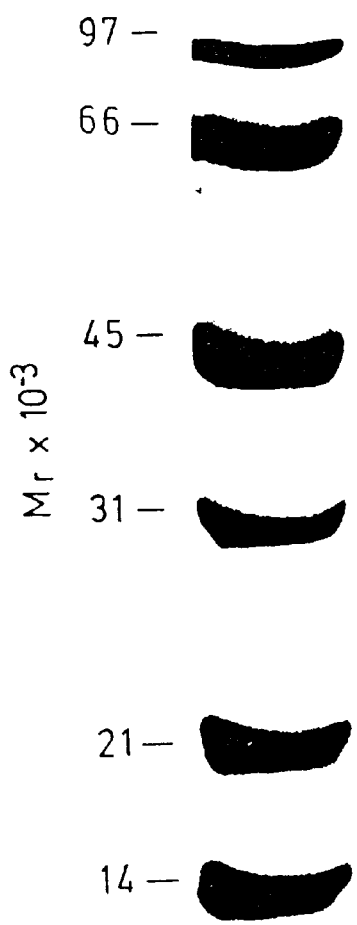

FIG. 6B. SDS Polyacrylamide Gel Electrophoresis of Purified Farnesyl:Protein Transferase. 0.7 μg of the peptide affinity-purified-column fraction (right lane) was subjected to SDS-10% polyacrylamide gel electrophoresis, and the protein bands were detected with a Coomassie Blue Stain. The molecular weights for marker protein standards (left lane) are indicated. Conditions of electrophoresis: 10% standard size gel run at 30 mA for 3 h.

Figure 7A:
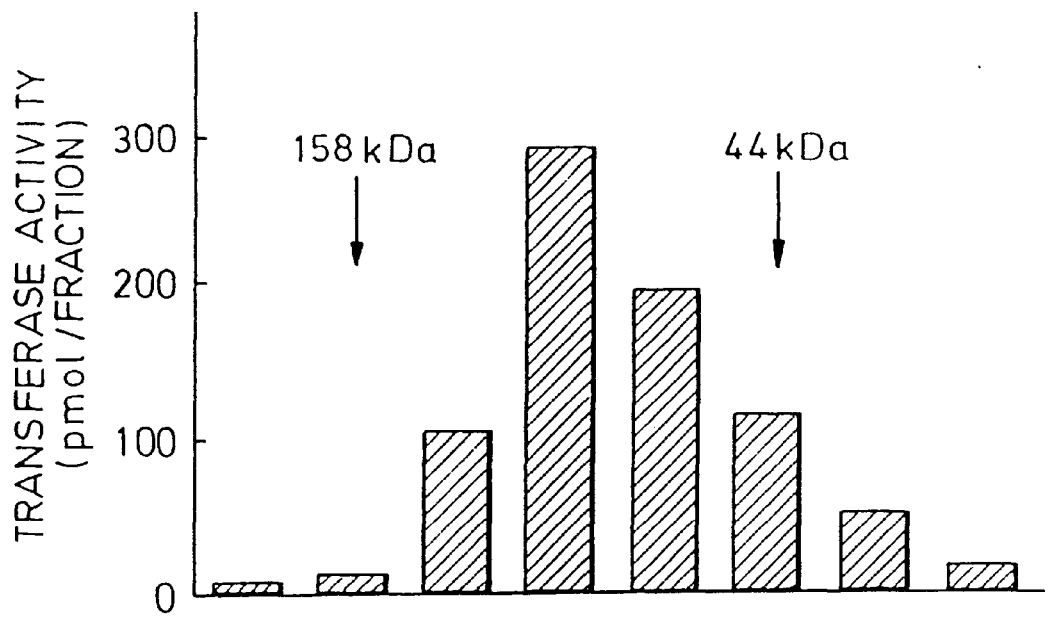
Figure 7B:
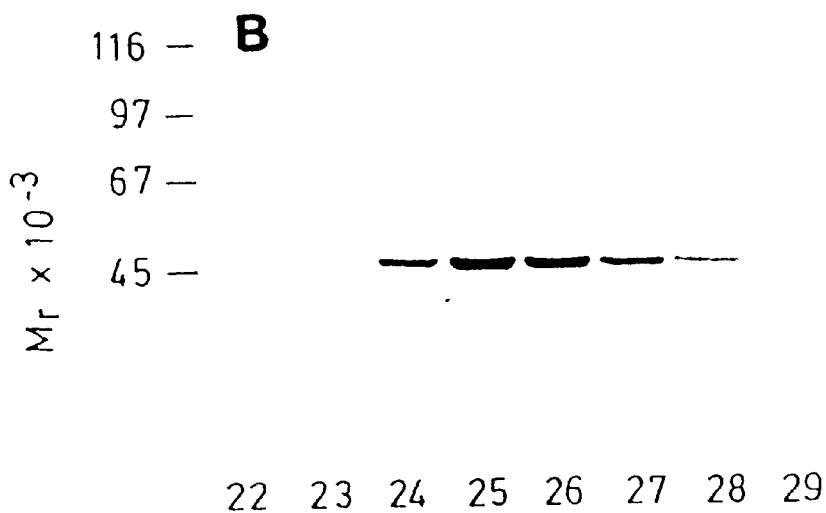

FIG. 7. Gel Filtration of Farnesyl:Protein Transferase. Affinity-purified farnesyl transferase (~1 µg protein) was subjected to gel filtration on a Superose-12 column (25× 0.5-cm) in 50 mM Tris-chloride (pH 7.5) containing 0.2 M NaCl, 1 mM DTT, and 0.2% octyl-β-D-glucopyranoside at a flow rate of 0.2 ml/min. Fractions of 0.5 ml were collected. Panel A, a 6-µl aliquot of each fraction was assayed for farnesyl:protein transferase activity by the standard method except that each reaction mixture contained 0.2% octyl-β-D-glucopyranoside. The column was calibrated with thyroglobulin (670 kDa), γ-globulin (158 kDa), ovalbumin (44 kDa), myoglobin (17 kDa), and vitamin B12 (1.35 kDa). Arrows indicate the elution position of the 158-kDa and 44-kDa markers. Panel B, a 0.42-ml aliquot of each fraction was concentrated to 40 µl with a Centricon 30 Concentrator (Amicon), and 25 µl of this material was then subjected to electrophoresis on an 10% SDS polyacrylamide gel. The gel was stained with silver nitrate and calibrated with marker proteins (far-right lane).

Figure 8:
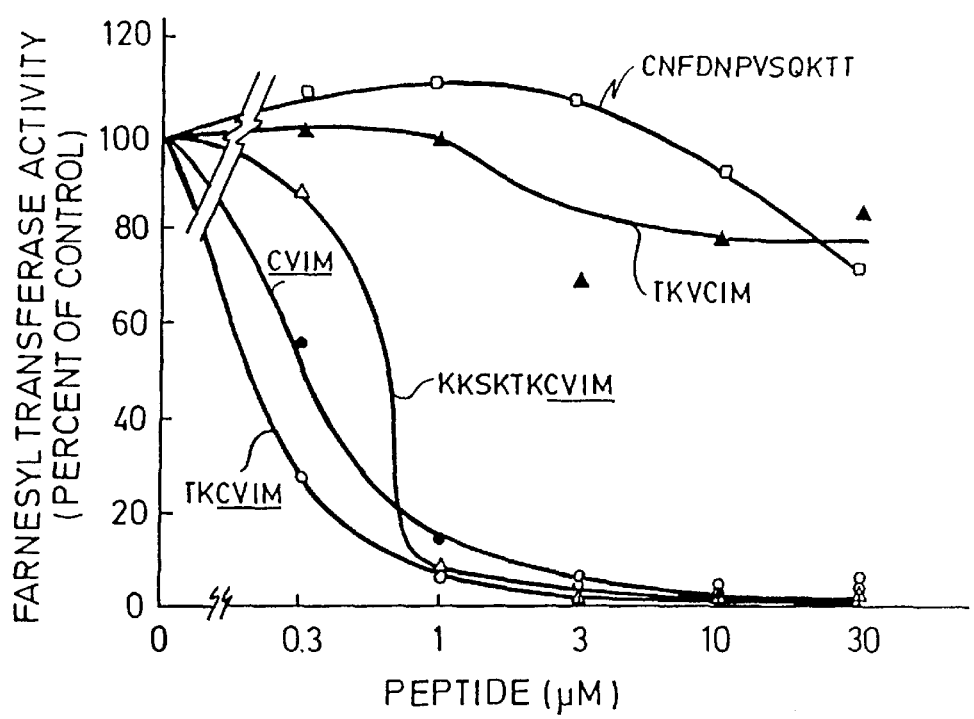

FIG. 8. Inhibition of Farnesyl:Protein Transferase Activity by Peptides. Each standard reaction mixture contained 10 pmol [$^3$H]FPP, 1.8 µg of partially purified farnesyl:protein transferase, 40 µM p21$^{H-ras}$, and the indicated concentration of competitor peptide added in 3 µl of 10 mM DTT. After incubation for 1 h at 37° C., TCA-precipitable radioactivity was measured as described in Experimental Procedures. Each value is the mean of triplicate incubations (no peptide) or a single incubation (+peptide). A blank value of 0.11 pmol/h was determined in a parallel incubation containing 20 mM EDTA. This blank was subtracted from each value before calculating "% of control" values. The "100% of control" value after subtraction of the blank was 3.78 pmol of [$^3$H]FPP p21$^{H-ras}$ formed per h. Peptides ∆, ○ and ● correspond to the COOH-terminal 10, 6, and 4 amino acids of wild-type human p21$^{H-ras}$ protein, respectively. Peptides □ and ▲ are control peptides.

Figure 9:
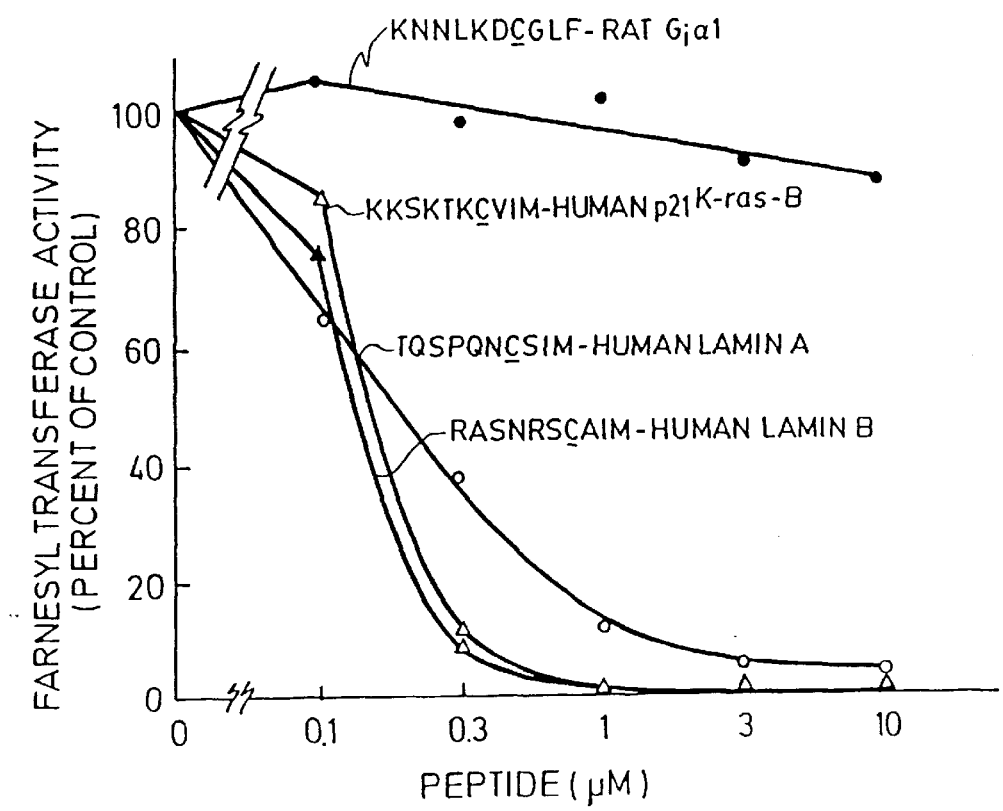

FIG. 9. Inhibition of Farnesyl:Protein Transferase Activity by Peptides. Incubations were carried out exactly as described in the legend to FIG. 8. The "100% of control value" was 2.92 pmol of [$^3$H]farnesyl p21$^{H-ras}$ formed per hour. The blank value was 0.20 pmol/h. Each peptide consisted of the COOH-terminal 10 residues of the indicated protein.

FIG. 10. Inhibition of Farnesyl:Protein Transferase By Tetrapeptide Analogues of CVIM. The standard assay mixture contained 15 pmol [$^3$H]FPP, 4 to 7.5 µg partially purified farnesyl transferase, 30 or 40 µM p21$^{H-ras}$, and the indicated concentration of competitor tetrapeptide. After 30 or 60 min, the amount of [$^3$H]farnesyl attached to p21$^{H-ras}$ was measured by trichloracetic acid precipitation as described in the methods section of Example II. Each value is the average of duplicate or triplicate incubations (no peptide) or a single incubation (+peptide). Each tetrapeptide was tested in a separate experiment together with equivalent concentrations of CVIM. The values for inhibition by CVIM (······) represent mean values from 21 experiments in which the mean "100% of control" value was 13 pmol min$^{-1}$mg protein$^{-1}$. K$_i$, concentration of tetrapeptide giving 50% inhibition CVIA is SEQ ID NO:18 and CVAM is SEQ ID NO:23.

Figure 11:
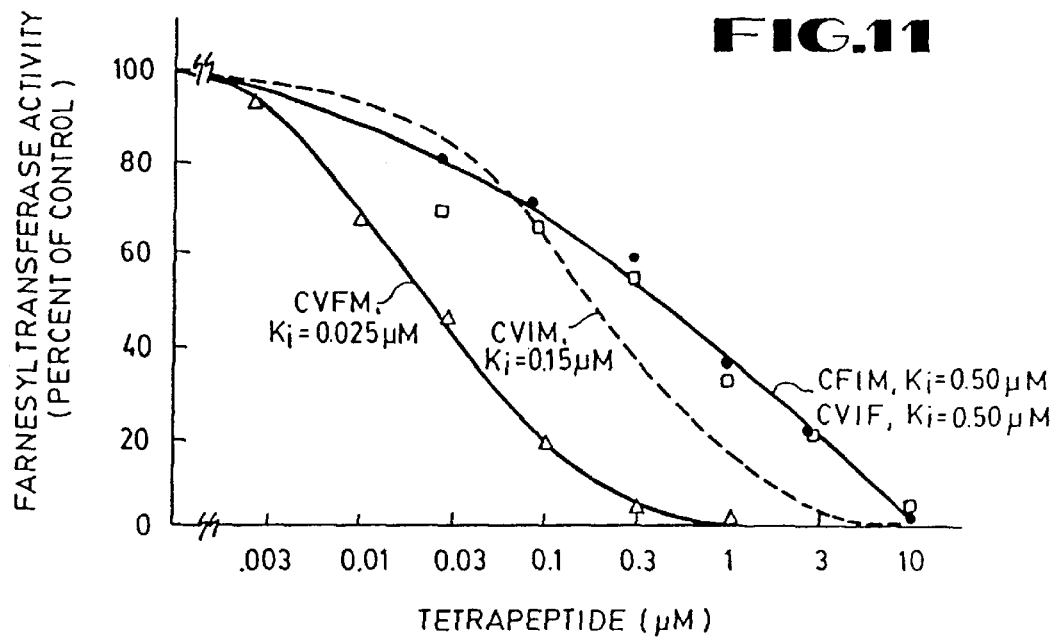

FIG. 11. Inhibition of Farnesyl:Protein Transferase Activity By Phenylalanine-containing Analogues of CVIM. Enzyme activity was measured in the presence of the indicated concentration of competitor tetrapeptide as described in the legend to FIG. 10 CVFM is SEQ ID NO:28, CFIM is SEQ ID NO:27 and CVIF is SEQ ID NO:29.

Figure 12A:
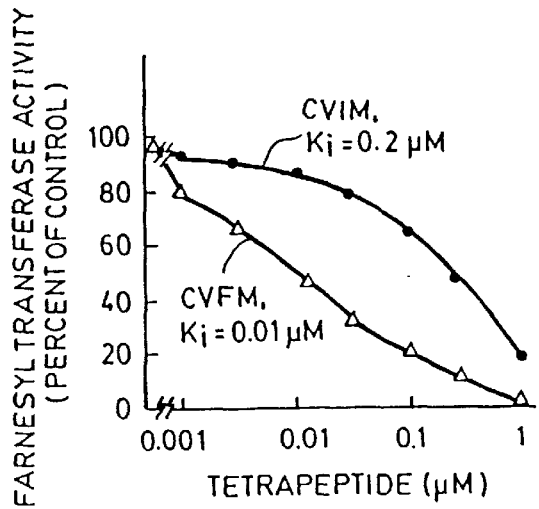
Figure 12B:
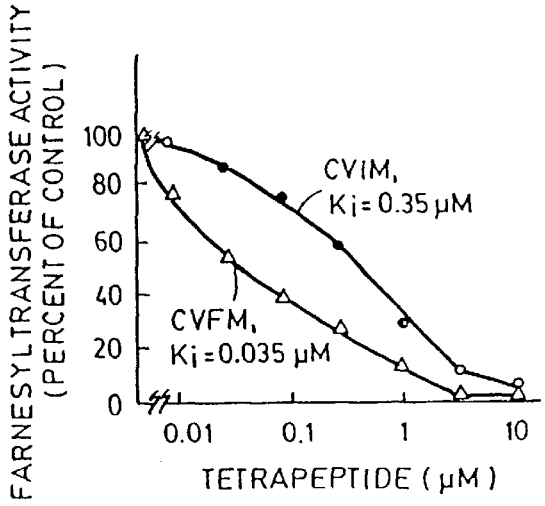

FIG. 12. Inhibition of Farnesylation of p21$^{H-ras}$ (A) and Biotinylated KTSCVIM (SEQ ID NO:41) (B) By CVFM (SEQ ID NO:28). Panel A: Each reaction mixture contained 15 pmol [$^3$H]FPP, 4.5 or 6 ng of purified farnesyl:protein transferase, 40 µM p21$^{H-ras}$, and the indicated concentration of competitor tetrapeptide. After incubation for 30 min at 37° C., the amount of [$^3$H]farnesyl transferred to p21$^{H-ras}$ was measured by the standard filter assay. Values shown are the average of two experiments. The "100% of control" values were 16 and 19 nmol min$^{-1}$ mg protein$^{-1}$, Panel B: Each reaction contained 15 pmol [$^3$H]FPP, 4.5 or 6 ng of purified farnesyl:protein transferase, 3.4 µM biotinylated KTSCVIM, and the indicated concentration of competitor tetrapeptide. After incubation for 30 min at 37° C., the [$^3$H]farnesyl-labeled peptide was trapped on streptavidin-agarose, washed, separated from the unincorporated [$^3$H] FPP, and subjected to scintillation counting. Values shown are the mean of 3 experiments. The "100% of control" values were 10, 17, and 21 nmol min$^{-1}$mg protein$^{-1}$.

FIG. 13. Inhibition of Farnesyl:Protein Transferase By Modified Tetrapeptides. Enzyme activity was measured in the presence of varying concentrations of the indicated tetrapeptide as described in the legend to FIG. 10. The "100% of control" values were 9.3 and 9.2 pmol min$^{-1}$ mg protein$^{-1}$ in Panels A and B, respectively.

Figure 14:
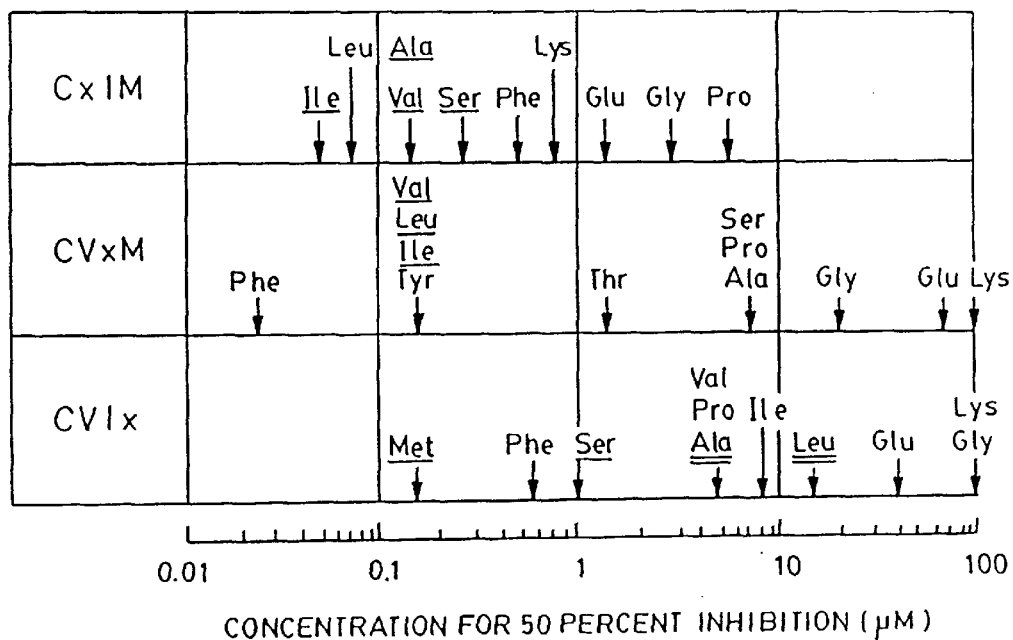

FIG. 14. Inhibition of Farnesyl:Protein Transferase By Tetrapeptides With Single Amino Acid Substitutions in CVIM. Enzyme activity was measured in the presence of the indicated competitor tetrapeptide as described in the legend to FIGS. 10 and 11. Each tetrapeptide was tested at seven different concentrations ranging from 0.01 to 100 µM. The concentration of tetrapeptide giving 50% inhibition was calculated from the inhibition curve. The single and double underlines denote tetrapeptides corresponding to the COOH-terminal sequence of mammalian and fungal proteins, respectively, that are candidates for farnesylation (see Table III).

Figure 15:
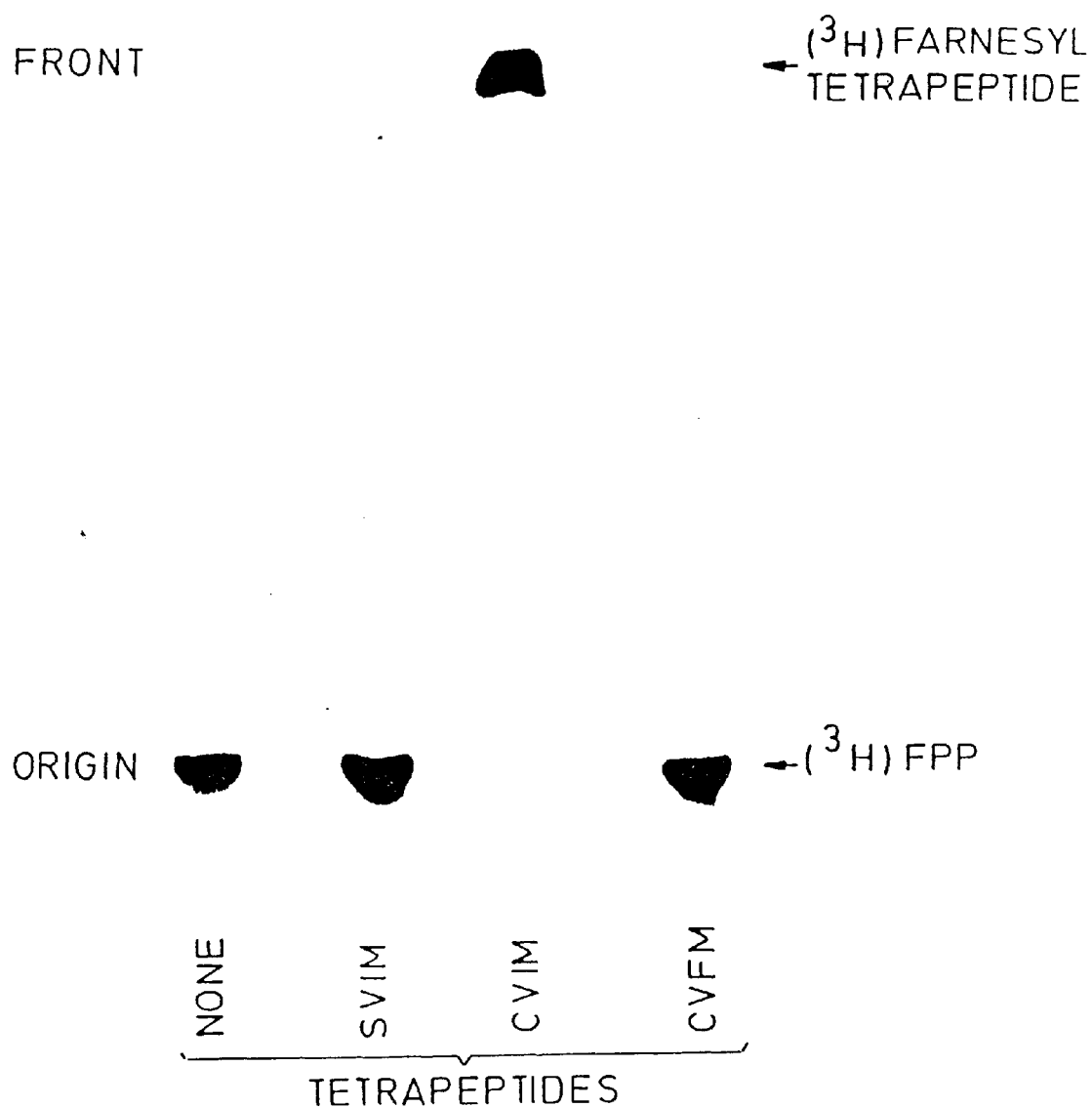

FIG. 15. Farnesylation of CVIM but not CVFM by purified farnesyl:protein transferase. The standard assay mixture (25 µl) contained 17 pmol [$^3$H]FPP (44,000 dpm/ pmol), 5 ng of purified farnesyl:protein transferase, 0.2% (w/v) octyl-β-D-glucoside, and 3.6 µM of the indicated tetrapeptide. After incubation for 15 min at 37° C., the entire reaction mixture was subjected to thin layer chromatography for 4 h on Polygram SIL G sheet (Brinkmann Instruments) in a solvent system containing N-propanol/concentrated NH$_4$OH/water (6:3:1). The TLC sheet was then dried, sprayed with ENHANCE Spray (Dupont-New England Nuclear) and exposed to Kodak X-OMAT AR Film XAR-5 for 25 h at −70° C. SVIM is SEQ ID NO:42 and CVFM is SEQ ID NO:28.

Figure 16:
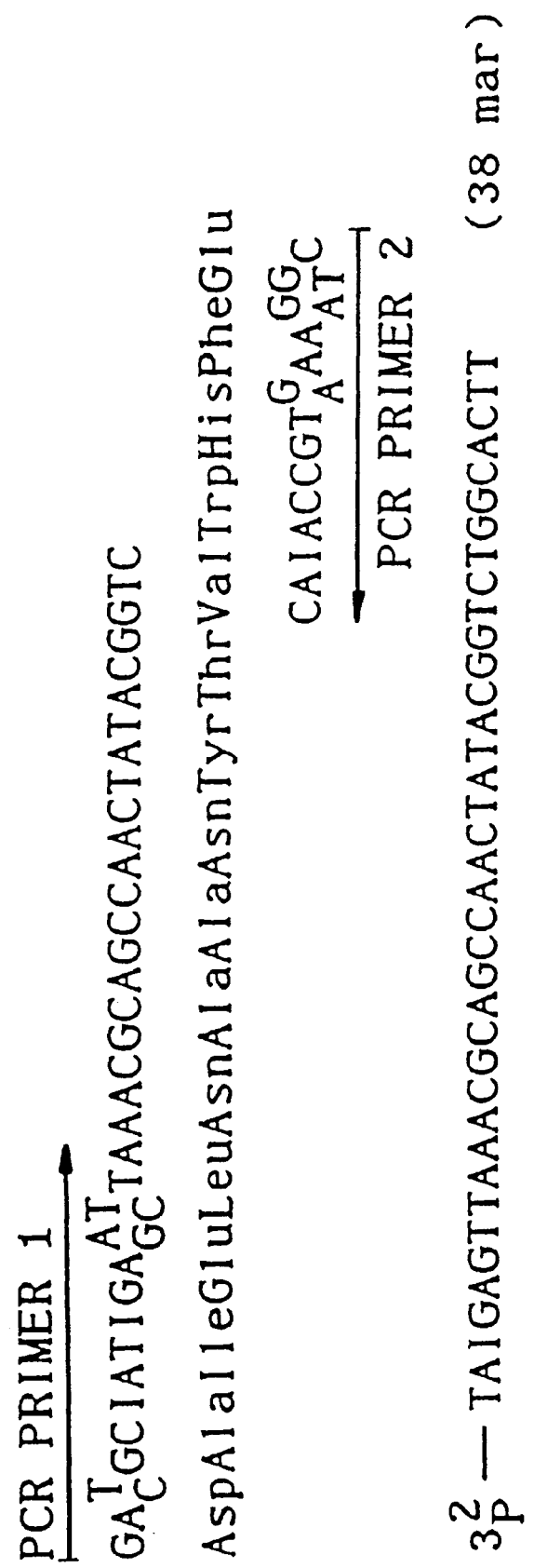

FIG. 16. A description of primers proposed for use in the cloning of the α subunit gene. In the Figure, Primer 1 is SEQ ID NO:43; Primer 2 is SEQ ID NO:45, reading in the direction of the arrow; the amino acid sequence is SEQ ID NO: 44; and the 38-mer is SEQ ID NO: 46.

Figure 17:
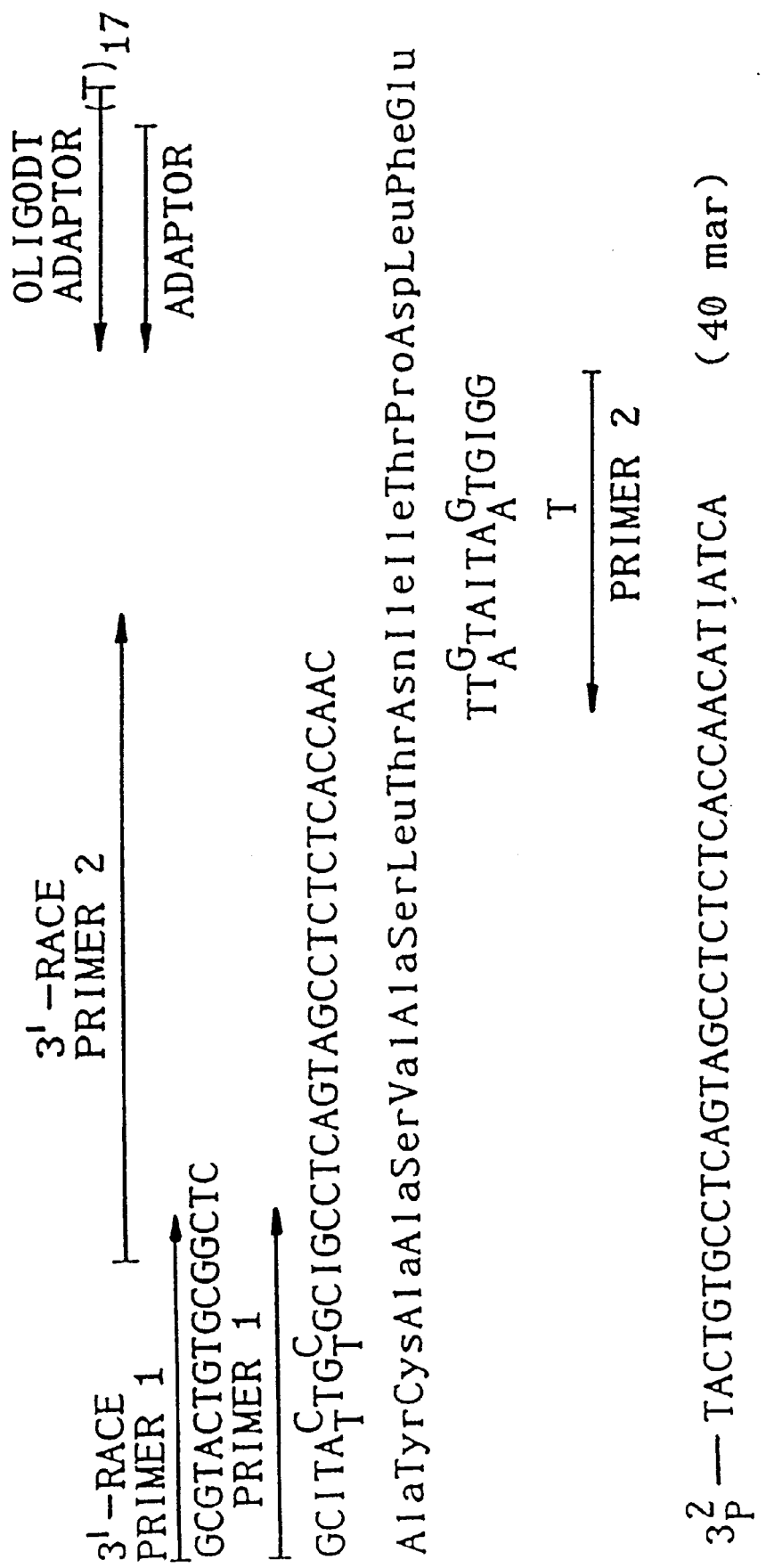

FIG. 17. A description of primers proposed for use in the cloning of the β subunit gene. In the Figure, Primer 1 is SEQ ID NO:47; the longer primer immediately below in the figure is SEQ ID NO: 48; Primer 2 is SEQ ID NO:49, reading in the direction of the arrow; the amino acid sequence is SEQ ID NO: 7; and the 40-mer is SEQ ID NO:50.

The following examples illustrate techniques discovered by the inventors for the identification and purification of farnesyl protein transferase enzyme, as well as techniques for its assay and for the screening of new compounds which may be employed to inhibit this enzyme. These studies also demonstrate a variety of peptidyl compounds which themselves can be employed to inhibit this enzyme. It should be appreciated by those of skill in the art that the techniques disclosed in the examples which follow represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Preparation and Characterization of Farnesyl:Protein Transference

1. Materials

Peptides were obtained from Peninsula Laboratories or otherwise synthesized by standard techniques. All peptides were purified on HPLC, and their identity was confirmed by amino acid analysis. Just prior to use, each peptide was dissolved at a concentration of 0.8 mM in 10 mM dithiothreitol (DTT), and all dilutions were made in 10 mM DTT. Unlabeled farnesyl pyrophosphate (FPP) was synthesized by the method of Davisson, et al. (13). [1-$^3$H]Farnesyl pyrophosphate (20 Ci/mmol) was custom synthesized by New England Nuclear. Geraniol and farnesol (both all-trans) were obtained from Aldrich Chemical. All-trans geranylgeraniol was a gift of R. Coates (University of Illinois).

Recombinant wild type human $p21^{H\text{-}ras}$ protein was produced in a bacterial expression system with pAT-rasH (provided by Channing J. Der, La Jolla Cancer Research Foundation, La Jolla, Calif.), an expression vector based on pXVR (14). The plasmid was transformed into *E. coli* JM105, and the recombinant $p21^{H\text{-}ras}$ protein was purified at 4° C. from a high speed supernatant of the bacterial extracts by sequential chromatography on DEAE-Sephacel and Sephadex G-75. Purity was ~90% as judged by Coomassie blue staining of SDS gels. Purified $p21^{H\text{-}ras}$ was concentrated to 15 mg/ml in 10 mM Tris-chloride (pH 7.5) containing 1 mM DTT, 1 mM EDTA, 3 mM MgCl$_2$, and 30 µM GDP and stored in multiple aliquots at −70° C.

2. Assay for Farnesyl:Protein Transferase Activity

Farnesyl:protein transferase activity was determined by measuring the amount of $^3$H-farnesol transferred from $^3$H]farnesyl pyrophosphate ([$^3$H]FPP) to $p21^{H\text{-}ras}$ protein. The standard reaction mixture contained the following concentrations of components in a final volume of 25 µl: 50 mM Tris-chloride (pH 7.5), 50 µM ZnCl$_2$, 20 mM KCl, 1 mM DTT, and 40 µM $p21^{H\text{-}ras}$. The mixture also contained 10 pmoles of [$^3$H]FPP (~30,000 dpm/pmol) and 1.8–3.5 µg of partially purified farnesyl:protein transferase (see below). After incubation for 1 h at 37° C. in 12×75-mm borosilicate tubes, the reaction was stopped by addition of 0.5 ml of 4% SDS and then 0.5 ml of 30% trichloroacetic acid (TCA).

The tubes were vortexed and left on ice for 45–60 min, after which 2 ml of a 6% TCA/2% SDS solution were added. The mixture was filtered on a 2.5-cm glass fiber filter with a Hoefer filtration unit (FH 225). The tubes were rinsed twice with 2 ml of the same solution, and each filter was washed five times with 2 ml of 6% TCA, dried, and counted in a scintillation counter. One unit of activity is defined as the amount of enzyme that transfers 1 pmol of [$^3$H]farnesol from [$^3$H]FPP into acid-precipitable $p21^{H\text{-}ras}$ per hour under the standard conditions.

3. Purification of Farnesyl:Protein Transferase

All steps were carried out at 4° C. except where indicated:

Step 1—Ammonium Sulfate Fractionation: Brains from 50 male Sprague-Dawley rats (100–150 g) were homogenized in 100 ml of ice-cold buffer containing 50 mM Tris-chloride (pH 7.5), 1 mM EDTA, 1 mM EGTA, 0.2 mM phenylmethylsulfonyl fluoride, and 0.1 mM leupeptin, and the extract was spun at 60,000×g for 70 min. The supernatant was brought to 30% saturation with solid ammonium sulfate, stirred for 30 minutes on ice, and centrifuged at 12,000×g for 10 min to remove precipitated proteins. The resulting supernatant was adjusted to 50% saturation with ammonium sulfate, and the resulting pellet was dissolved in ~20 ml of 20 mM Tris-chloride (pH 7.5) containing 1 mM DTT and 20 µM ZnCl$_2$ and dialyzed for 4 hours against 4 liters of the same buffer and then 4 liters of fresh buffer of the same composition for 12 h. The dialyzed material was divided into multiple aliquots and stored at −70° C.

Step 2—Ion-exchange Chromatography: A portion of the 30–50% ammonium sulfate fraction (200 mg protein) was chromatographed on a Mono Q 10/10 column using an FPLC system (Pharmacia LKB Biotechnology). The column was run as described in the legend to FIG. 5. Fractions eluting between 0.3 and 0.4 M NaCl contained the majority of the transferase activity. These fractions were pooled, divided into multiple aliquots, and stored at −70° C.

Step 3—Affinity Chromatography: An affinity column containing a peptide corresponding to the COOH-terminal six amino acids of $p21^{K\text{-}ras\text{-}B}$ protein was prepared as follows. Fifteen mg of the peptide TKCVIM were coupled to 1 g of activated CH-Sepharose 4B (Pharmacia LKB Biotechnology) according to the manufacturer's instructions. The resulting 2.5-ml slurry was poured into a column, and excess uncoupled peptide was removed by 10 cycles of alternating washes, each consisting of 40 column volumes of 0.1 M sodium acetate (pH 4.0) and then 0.1 M Tris-chloride (pH 8.0). Both buffers contained 1 M NaCl and 10 mM DTT. The column was stored at 4° C. in 20 mM Tris-chloride (pH 7.2) and 0.02% sodium azide. Fifteen mg of Mono Q-purified material in 10 ml were applied to a 1-ml peptide column equilibrated in 50 mM Tris-chloride (pH 7.5) containing 0.1 M NaCl and 1 mM DTT (Buffer A). The enzyme-containing solution was cycled through the column three times at room temperature. The column was washed with 20 ml of Buffer A containing 0.2% (w/v) octyl-β-D-glucopyranoside (Buffer B). The enzyme was eluted with 20 ml of 50 mM Tris-succinate (pH 5.0) containing 1 mM DTT, 0.1 M NaCl, and 0.2% octyl-β-D-glucopyranoside. The pH 5 eluate was concentrated and washed twice with a 10-fold excess of Buffer B in a CF25 Centriflo ultrafiltration cone (Amicon) and brought to 1 ml (10-fold concentration relative to the starting material).

Step 4—Gel Filtration: Affinity-purified farnesyl transferase (~1 µg) was chromatographed on a Superose 12 column as described in the legend to FIG. 7.

In the enzyme characterization experiments of FIGS. 1–4, 8, and 9, a partially purified fraction of farnesyl:protein transferase was used. This enzyme was prepared by Steps 1 and 2 as described above, after which 6 mg of the Mono Q-purified material was concentrated to 2 ml and then loaded onto a 1.6×50-cm Sephacryl S-200 high resolution gel filtration column (Pharmacia LKB Biotechnology). The column was equilibrated with 50 mM Tris-chloride (pH 7.5) containing 1 mM DTT, 0.2 M NaCl, 20 µM ZnCl$_2$, and 0.2% octyl-β-glucopyranoside and eluted with the same buffer at a flow rate of 15 ml/h. Only the peak fraction, containing 1 mg protein and 40% of initial activity, was used for studies.

4. Identification of $^3$H-Isoprenoid Transferred from [$^3$H]FPP

A modification of the procedure described by Casey et al. (ref. 6) was employed as follows: Briefly, two standard transferase reactions of 25-μl each were conducted for 1 hour at 37° C. The mixtures were then pooled, and a 25-μl aliquot from the 50-μl pooled sample was diluted to 250 μl with 2% (w/v) SDS. This mixture was precipitated with an equal volume of 30% TCA, filtered through nitrocellulose, (7 mm disc), washed twice with 250 μl 6% TCA/2% SDS followed by five washes with 5% TCA, digested with 8 μg trypsin, and subjected to cleavage with methyl iodide. The released $^3$H-isoprenoids were extracted into chloroform/methanol and chromatographed on a reverse-phase HPLC system as described in the legend to FIG. 4.

5. Other Methods

SDS polyacrylamide gel electrophoresis was carried out as described by Laemmli (16). Gels were calibrated with high range SDS-PAGE standards (Bio-Rad). Protein content of extracts was measured by the method of Lowry, et al. (17) except for that of the affinity-purified material, which was estimated by comparison to the bovine serum albumin marker ($M_r$ 66,000) following SDS gel electrophoresis and Coomassie staining.

6. Discussion

As an initial attempt to identify a farnesyl protein transferase enzyme, rat brain cytosol was fractionated with ammonium sulfate and the active fraction subjected to ion exchange chromatography on a Mono Q column followed by gel filtration on Sephacryl S-200. FIG. 1 shows that the active fraction from this column incorporated radioactivity from [$^3$H]farnesol into trichloroacetic acid precipitable p21$^{H-ras}$ in a time-dependent fashion at 37° C. The incorporated radioactivity could be visualized as a band of the expected molecular weight of −21 kDa on SDS polyacrylamide gels (inset). The concentration of [$^3$H]farnesyl pyrophosphate that gave half-maximal reaction velocity was approximately 0.5 μM (FIG. 2A). The half-maximal concentration for p21$^{H-ras}$ was approximately 5 μM, and there was no difference when the p21$^{H-ras}$ was equilibrated with a nonhydrolyzable GTP or ATP analogue or with GDP (FIG. 2B).

With p21$^{H-ras}$ as a substrate, the transferase reaction was inhibited by 0.15 mM EDTA, and this inhibition was reversed by 0.1 to 1.0 mM concentrations of zinc or magnesium chloride (FIG. 3). At higher concentrations of zinc chloride, inhibition was observed.

To confirm that the transferred material was [$^3$H]farnesol, the washed trichloracetic acid-precipitated material was digested with trypsin, the radioactivity released with methyl iodide, and the products subjected to reverse-phase HPLC. The methyl iodide-released material co-migrated with an authentic standard of all-trans farnesol ($C_{15}$) (FIG. 4A). Some radioactivity emerged from the column prior to the geranol standard ($C_{10}$), but this was the same in the presence and absence of methyl iodide treatment. This early-eluting material was believed to represent some tryptic peptides whose radioactivity was not released by methyl iodide.

FIG. 5 shows the elution profile of farnesyl transferase activity from a Mono Q column. The activity appeared as a single sharp peak that eluted at approximately 0.35 M sodium chloride.

The peak fractions from the Mono Q column were pooled and subjected to affinity chromatography on a column that contained a covalently-bound peptide corresponding to the carboxyl-terminal 6-amino acids of p21$^{K-rasB}$. All of the farnesyl transferase activity was adsorbed to the column, and about 50% of the applied activity was recovered when the column was eluted with a Tris-succinate buffer at pH 5.

Table II summarizes the results of a typical purification procedure that started with 50 rat brains. After ammonium sulfate precipitation, mono Q chromatography, and affinity chromatography, the farnesyl transferase was purified approximately 61,000-fold with a yield of 52%. The final specific activity was about 600,000 units/mg.

TABLE II

PURIFICATION OF FARNESYL:PROTEIN TRANSFERASE FROM RAT BRAIN

| Fraction | Protein mg | Specific Activity units/mg | Total Activity units | Purification-fold | Recovery % |
|---|---|---|---|---|---|
| 30–50% Ammonium Sulfate | 712 | 9.7$^a$ | 6906 | 1 | 100 |
| Mono Q | 30 | 275 | 8250 | 28 | 119 |
| Affinity Column | 0.006$^b$ | 600,000 | 3600 | 61,855 | 52 |

The purification procedure was started with 50 rat brains.
$^a$One unit of enzyme activity is the amount of enzyme that transfers 1 pmol of [$^3$H]farnesol from [$^3$H]FPP into acid-precipitable p21$^{H-ras}$ per h under the standard conditions.
$^b$Protein concentration was estimated by coomassie blue staining of a SDS polyacrylamide gel using various amounts (0.5 to 2 μg) of bovine serum albumin as a reference standard.

FIG. 6A shows the SDS gel electrophoretic profile of the proteins at each stage of this purification as visualized by silver staining. The peptide affinity column yielded a single protein band with an apparent subunit molecular weight of 50,000. When the purified enzyme was subjected to SDS gel electrophoresis under more sensitive conditions, the 50-kDa protein could be resolved into two closely spaced bands that were visualized in approximately equimolar amounts (FIG. 6B).

To confirm that the 50-kDa band was the farnesyl transferase enzyme, the affinity column purified material was subjected to gel filtration. FIG. 7 shows that the farnesyl transferase activity and the 50-kDa band co-eluted from this column at a position corresponding to an apparent molecular weight of 70–100 kDa as determined from the behavior of markers of known molecular weight.

The adherence of the farnesyl transferase to the peptide affinity column suggested that the enzyme was capable of recognizing short peptide sequences. To test for the specificity of this peptide recognition, the ability of various peptides to compete with p21$^{H-ras}$ for the farnesyl transferase activity was measured. The peptide that was used for affinity chromatography corresponded to the carboxyl terminal six amino acids of P21$^{K-rasB}$ (TKCVIM). As expected, this peptide competitively inhibited farnesylation of P21$^{H-ras}$ (open circles in FIG. 8). The terminal 4-amino acids in this sequence (CVIM) (closed circles) were sufficient for competition. These two short peptides were no less effective than a peptide that contained the final 10-amino acids of the sequence (KKSKTKCVIM) (open triangles). The simple transposition of the cysteine from the fourth to the third position from the COOH-terminus of the hexapeptide (TKVCIM) (closed triangles) severely reduced inhibitory activity. An irrelevant peptide (closed squares) also did not inhibit.

FIG. 9 compares the inhibitory activities of four peptides of 10-amino acids each, all of which contain a cysteine at the fourth position from the COOH-terminus. The peptides corresponding to the COOH-terminus of human p21$^{K-rasB}$ and human lamin A and lamin B all inhibited farnesylation. All of these peptides are known to be prenylated in vivo (6, 15). On the other hand, the peptide corresponding to the sequence of rat Giα1, a 40-kDa G protein that does not appear to be farnesylated in vivo (Casey, P., unpublished observations), did not compete for the farnesyl transferase reaction.

In data not shown it was found that the 10-amino acid peptide corresponding to the COOH-terminus of $p21^{H\text{-}ras}$ (CVIS), $p21^{N\text{-}ras}$ (CVVM), and $p21^{H\text{-}rasA}$ (CIIM) all competed for the farnesylation reaction.

EXAMPLE II

Further Characterization of Farnesyl:Protein Transferase

In the present Example, a series of tetrapeptides were tested for their ability to bind to the rat brain $p21^{H\text{-}ras}$ farnesyl:protein transferase as estimated by their ability to compete with $p21^{H\text{-}ras}$ in a farnesyl transfer assay. Peptides with the highest affinity had the structure Cys-A1-A2-X, where A1 and A2 are aliphatic amino acids and X is a C-terminal methionine, serine, or phenylalanine. Charged residues reduced affinity slightly at the A1 position and much more drastically at the A2 and X positions. Effective inhibitors included tetrapeptides corresponding to the COOH-termini of all animal cell proteins known to be farnesylated. In contrast, the tetrapeptide CAIL, which corresponds to the COOH-terminus of the only known examples of geranylgeranylated proteins (neural G protein γ subunits) did not compete in the farnesyl transfer assay, suggesting that the two isoprenes are transferred by different enzymes. A biotinylated hexapeptide corresponding to the COOH-terminus of $p21^{K\text{-}rasB}$ was farnesylated, suggesting that at least some of the peptides serve as substrates for the transferase. The data are consistent with a model in which a hydrophobic pocket in the farnesyl:protein transferase recognizes tetrapeptides through interactions with the cysteine and the last two amino acids.

1. Materials and Methods
a. Peptides

Peptides were prepared by established procedures of solid-phase synthesis (18) Tetrapeptides were synthesized on the Milligen 9050 Synthesizer using Fmoc chemistry. After deprotection of the last residue, a portion of the resin was used to make the N-acetyl-modified version of CVIM. This was done off-line in a solution of acetic anhydride and dimethylformamide at pH 8 (adjusted with diisopropylethylamine). The acetylated and unacetylated peptides were cleaved with 50 ml of trifluoroacetic acid-:phenol (95:5) plus approximately 1 ml of ethanedithiol added as a scavenger. The N-octyl-modified version of CVIM was synthesized on an Applied Biosystems Model 430 Synthesizer using tBoc chemistry. The octyl group was added in an amino acid cycle using octanoic acid. The peptide was cleaved from the resin at 0° C. with a 10:1:1 ratio of HF (mls):resin (g):anisole (ml). The peptides were purified by high pressure liquid chromatography (HPLC) on a Beckman C18 reverse phase column (21.1 cm×15 cm), eluted with a water-acetonitrile gradient containing 0.1% (v/v) trifluouroacetic acid. Identity was confirmed for all peptides by fast atom bombardment (FAB) mass spectrometry. Just prior to use, each peptide was dissolved at a concentration of 0.8 mM in 10 mM dithiothreitol (DTT), and all dilutions were made in 10 mM DTT.

Biotinylated KTSCVIM was synthesized on an Applied Biosystems 430A Synthesizer. The biotin group was added after removal of the N-terminal protecting group before cleavage of the peptide from the resin. Specifically, a 4-fold molar excess of biotin 4-nitrophenyl ester was added to the 0.5 g resin in 75 ml dimethylformanide at pH 8 and reacted for 5 h at room temperature. Cleavage, identification, and purification were carried out as described above.

To synthesize S-acetoamido CVIM, purified CVIM was dissolved at a final concentration of 1 mM in 0.1 ml of 0.5 M Tris-chloride (pH 8.0) containing 15 mM DTT. The tube was flushed with nitrogen for 2 min, sealed, and incubated for 2.5 h at 37° C. to reduce the cysteine residue, after which iodoacetamide was added to achieve a final concentration of 35 mM. After incubation for 15 min at 37° C., the reaction was stopped by addition of 10 mM DTT. Complete alkylation of CVIM was confirmed by FAB spectrometry and HPLC. The molecular weight of the product corresponded to the expected molecular mass of S-acetoamido CVIM.

b. Assay for Farnesyl:Protein Transferase

The standard assay involved measuring the amount of [$^3$H]farnesyl transferred from all-trans [$^3$H]FPP to recombinant human $p21^{H\text{-}ras}$ as described in Example I. Each reaction mixture contained the following concentrations of components in a final volume of 25 μl: 50 mM Tris-chloride (pH 7.5), 50 μM $ZnCl_2$, 30 mM KCl, 1 mM DTT, 30 or 40 μM $p21^{H\text{-}ras}$, 15 pmol [$^3$H]FPP (12–23,000 dpm/pmol), 4 to 7.5 μg of partially purified farnesyl:protein transferase (Mono Q fraction, see Example I), and the indicated concentration of competitor peptide added in 3 μl of 10 mM DTT. After incubation for 30–60 min at 37° C., the amount of [$^3$H]farnesyl present in trichloroacetic acid-precipitable $p21^{H\text{-}ras}$ was measured by a filter assay as described in Example I. A blank value (<0.6% of input [$^3$H]FPP) was determined in parallel incubations containing no enzyme. This blank value was subtracted before calculating "% of control" values.

c. Transfer of [$^3$H]Farnesyl from [$^3$H]FPP to Biotinylated KTECVIM Peptide

This assay takes advantage of the fact that peptides containing the Cys-AAX motif of ras proteins can serve as substrates for prenylation by farnesyl transferase. A heptapeptide containing the terminal four amino acids of $p21^{K\text{-}rasB}$ was chosen as a model substrate since it has a 20 to 40-fold higher affinity for the enzyme than does the COOH-terminal peptide corresponding to $p21^{H\text{-}ras}$. A biotinylated peptide is used as substrate so that the reaction product, [$^3$H]farnesylated peptide, can be trapped on a solid support such as streptavidinagarose. The bound [$^3$H]farnesylated peptide can then be washed, separated from unincorporated [$^3$H]FPP, and subjected to scintillation counting.

The biotin-modified KTSCVIM is synthesized on an Applied Biosystems 430A Synthesizer using established procedures of solid phase peptide synthesis. The biotin group is added after deprotection of lysine and before cleavage of the peptide from the resin. The identity and purity of the biotinylated peptide is confirmed by quantitative amino acid analysis and fast atom bombardment (FAB) mass spectrometry.

An aliquot of biotinylated KTSCVIM (0.4 mg) is dissolved in 0.6 ml of 10 mM sodium acetate (pH 3) buffer containing 1 mM DTT and 50% ethanol to give a final concentration of 0.67 mg/ml or 601 μM. This solution can be stored at 4° C. for at least 1 month. Immediately prior to use, the peptide solution is diluted with 1 mM DTT to achieve a peptide concentration of 18 μM. The standard reaction mixture contains the following components in a final volume of 25 μl: 50 mM Tris-chloride (pH 7.5), 50 μM $ZnCl_2$, 20 mM KCl, 1 mM DTT, 0.2% (v/v) octyl-β-glucopryranoside, 10–15 pmol of [³H]FPP (15–50,000 dpm/pmol), 3.6 μM biotinylated KTSCVIM, and 2–4 units of enzyme. After incubation at 37° C. for 30–60 min in 0.5-ml siliconized microfuge tubes, the reaction is stopped by addition of 200 μl of 20 mM Tris-chloride (pH 7.5) buffer containing 2 mg/ml bovine serum albumin, 2% SDS, and 150 mM NaCl. A 25-μl aliquot of well mixed streptavidin-agarose (Bethesda Research Laboratories, Cat. No. 5942SA) is then added, and the mixture is gently shaken for 30 min at room temperature to allow maximal binding of the [³H] farnesylated peptide to the beads.

The beads are then collected by spinning the mixture for 1 min in a microfuge (12,500 rpm). The supernatant is removed, and the beads are washed three times with 0.5 ml of 20 mM Tris-chloride (pH 7.5) buffer containing 2 mg/ml bovine serum albumin, 4% SDS, and 150 mM NaCl. The pellet is resuspended in 50 μl of the same buffer and transferred to a scintillation vial using a 200-μl pipettor in which the tip end has been cut off at an angle. The beads remaining in the tube are collected by rinsing the tube with 25 μl of the above buffer and adding it plus the pipettor to the vial. A blank value, which consists of the radioactivity adhering to the beads in parallel incubations containing no enzyme, should be less than 0.5% of the input [³H]FPP.

2. Results

To screen peptides for their affinity for the farnesyl:protein transferase, studies were conducted wherein the ability of the peptides to compete with $p21^{H-ras}$ for acceptance of [³H]farnesyl from [³H]FPP as catalyzed by a partially purified rat brain farnesyl:protein transferase was tested. As a reference point for the peptides, the tetrapeptide CVIM corresponding to the COOH-terminal sequence of $p21^{K-rasB}$ was employed. FIG. 10 shows a series of typical experiments in which alanine (Panel A), lysine (Panel B), or leucine (Panel C) was systematically substituted at each of the three positions following cysteine in CVIM. In each experiment the results were compared with those obtained with CVIM. Alanine and lysine were tolerated only at the A1 position. Insertion of these amino acids at the A2 or X positions decreased the affinity for the enzyme by more than 30-fold as estimated by the concentration required for 50% inhibition. Leucine was tolerated at the A2 position, but it decreased the affinity when inserted at the X position.

The substitution of phenylalanine for isoleucine at the A2 position increased the affinity for the enzyme by 6-fold, with half-maximal inhibition occurring at 25 nM (FIG. 11). No such effect was observed when phenylalanine was inserted at either of the other two positions.

In addition to performing assays with $p21^{H-ras}$ as a substrate, assays were also performed in which the substrate was a biotinylated heptapeptide, KTSCVIM, which contains the COOH-terminal four amino acids of $p21^{H-rasB}$ (2). The biotin was attached to the NH₂-terminus by coupling to the resin-attached peptide. The [³H]farnesylated product was isolated by allowing it to bind to beads coated with streptavidin as described in section c. above.

FIG. 12 shows that the peptide CVFM was more potent than CVIM when either $p21^{H-ras}$ or the biotinylated heptapeptide was used as acceptor (Panels A and B, respectively). In contrast to the other studies, which were conducted with a partially purified enzyme, the studies of FIG. 12 were carried out with a homogeneous preparation of affinity-purified farnesyl:protein transferase.

Figure 13A:
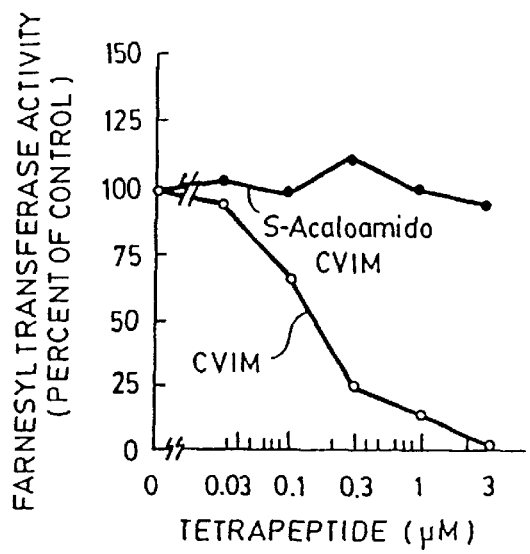
Figure 13B:
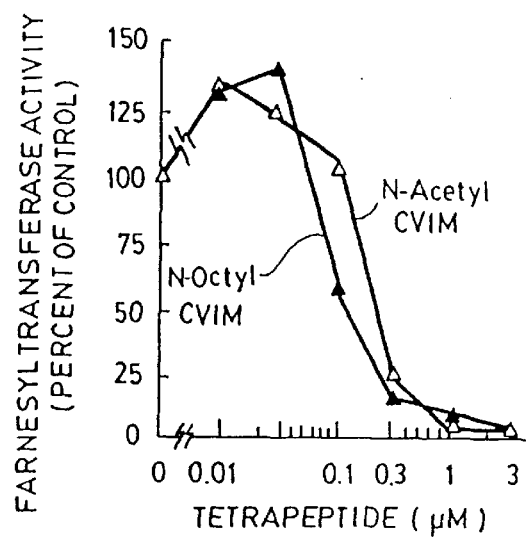

The free sulfhydryl group for the cysteine is likely required for tetrapeptide inhibition, as indicted by the finding that derivitization with iodoacetamide abolished inhibitory activity (FIG. 13A). A blocked NH₂-terminus is not required, as indicated by similar inhibitory activity of N-acetyl CVIM and N-octyl CVIM (FIG. 13B) as compared to that of CVIM (FIG. 13A).

FIG. 14 summarizes the results of all competition assays in which substitutions in the CVIM sequence were made. The results are presented in terms of the peptide concentration required for 50% inhibition. Table III summarizes the results of other experiments in which tetrapeptides corresponding to the COOH-termini of 19 proteins were studied, many of which are known to be farnesylated. The implications of these studies are discussed below in Section 3.

TABLE III

Inhibition of Rat Farnesyl: Protein Transferase by COOH-Terminal Tetrapeptides Corresponding to Known Proteins

| Protein | Species | COOH-Terminal Tetrapeptide | Concentration for 50% Inhibition μM |
|---|---|---|---|
| *$p21^{K-rasB}$ | Human, mouse | CVIM | 0.15 |
| *$p21^{K-rasA}$ | Human | CIIM | 0.15 |
| $p21^{N-ras}$ | Human | CVVM | 0.15 |
| $p21^{N-ras}$ | Mouse | CVLM | 0.15 |
| *Lamin B | Human, Xenopus laevis | CAIM | 0.15 |
| Lamin A | Human, Xenopus laevis | CSIM | 0.20 |
| Retinal cGMP phosphodiesterase, α-subunit | Bovine | CCVQ (SEQ ID NO:13) | 0.35 |
| *ras1 | S. cerevisciae | CIIC (SEQ ID NO:14) | 0.35 |
| *ras2 | S. cerevisciae | CIIS (SEQ ID NO:15) | 0.35 |
| *γ-Subunit of transducin | Bovine | CVIS (SEQ ID NO:16) | 1.0 |
| $p21^{H-ras}$ | Chicken | CVIS (SEQ ID NO:16) | 1.0 |
| $p21^{H-ras}$ | Human, rat | CVLS (SEQ ID NO:17) | 3.0 |

TABLE III-continued

Inhibition of Rat Farnesyl: Protein Transferase by COOH-Terminal Tetrapeptides Corresponding to Known Proteins

| Protein | Species | COOH-Terminal Tetrapeptide | Concentration for 50% Inhibition μM |
|---|---|---|---|
| *a-Mating factor | S. cerevisciae | CVIA (SEQ ID NO:18) | 5.0 |
| rap2b | Human | CVIL | 11 |
| Dras | Dictostelium | CLIL (SEQ ID NO:20) | 17 |
| rap1a/krev1 | Human | CLLL (SEQ ID NO:21) | 22 |
| *Mating factor | R. Toruloide | CTVA (SEQ ID NO:22) | 30 |
| γ-Subunit of G protein | Bovine | CAIL (SEQ ID NO:51) | 100 |
| HMG CoA reductase-1 | S. cerevisciae | CIKS (SEQ ID NO:52) | 100 |

Enzyme activity was measured in the presence of the indicated tetrapeptide as described in the legend to FIG. 10. Each tetrapeptide was tested at seven different concentrations ranging from 0.03 to 100 μM. The concentration giving 50% inhibition was calculated from the inhibition curve.
*Shown to be farnesylated in vivo.

3. Discussion

The current data extend the observations on the p21$^{ras}$ farnesyl:protein transferase set forth in Example I, and further indicate that the recognition site for this enzyme is restricted to four amino acids of the Cys-A1-A2-X type. As a reference sequence for these studies, the peptide CVIM was used. This peptide inhibited the farnesyl:protein transferase by 50% at a concentration of 0.15 μM. Substitution of various amino acids into this framework yielded peptides that gave 50% inhibitions at a spectrum of concentrations ranging from 0.025 μM (CVFM) to greater than 50 μM (FIG. 14).

In general, the highest inhibitory activities were achieved when the A1 and A2 positions were occupied with nonpolar aliphatic or aromatic amino acids. This stringency was more severe at the A2 than at the A1 position. Thus, peptides containing lysine or glutamic acid at the A1 position gave 50% inhibition at 0.7 and 1.5 μM, respectively. When these two residues were inserted at the A2 position, the affinity for the enzyme declined by more than 50-fold. Glycine and proline lowered inhibitory activity moderately at the A1 position (50% inhibition at 4 and 8 μM) and somewhat more severely at the A2 position (8 and 20 μM).

The X position showed the highest stringency. In the context of CVIX, methionine was the preferred residue but phenylalanine and serine were tolerated with only modest losses in activity (0.5 and 1 μM, respectively). Aliphatic resides and proline were disruptive at this position, with 50% inhibitions in the range of 5–11 μM. Glutamic acid, lysine, and glycine were not tolerated at all; 50% inhibition required concentrations above 40 μM.

A study of tetrapeptides corresponding to the COOH-termini of known proteins (Table III) gave results that were generally in keeping with those obtained with the substituted CVIM peptides. They provided the additional information that glutamine and cysteine are well tolerated at the X position (CCVQ (SEQ ID NO:13) and CIIC (SEQ ID NO:14). All of the proteins that are known to be farnesylated in intact cells (indicated by the asterisks in Table III) followed the rules outlined above, and all inhibited farnesylation at relatively low concentrations (5 μM or below) with the exception of the CTVA (SEQ ID NO:22) sequence, which is found in the mating factor of R. toruloides (19). This peptide inhibited the rat brain farnesyl:protein transferase by 50% only at the high concentrations of 30 μM. It is likely that the farnesyl:protein transferase in this fungal species has a different specificity than that of the rat brain.

The peptide CAIL (SEQ ID NO:51), which corresponds to the COOH-terminus of the γ-subunit of bovine brain G proteins (20,21), did not compete efficiently with p21$^{H-ras}$ for farnesylation (Table III). A 50% inhibition at the highest concentration tested (100 μM) was observed. The inhibitory activity was lower than that of CVIL (12 μM) or CAIM (0.15 μM). Thus, the combination of alanine at the A1 position and leucine at the X position is more detrimental than either single substitution. This finding is particularly relevant since the gamma subunit of G proteins from human brain (22) and rat PC12 cells (23) have been shown to contain a geranylgeranyl rather than a farnesyl. These findings suggest the existence of a separate geranylgeranyl transferase that favors CAIL (SEQ ID NO: 51) and perhaps other related sequences.

The studies with the biotinyated heptapeptide (FIG. 12B) confirm that at least some of the short peptides act as substrates for the enzyme. The saturation curves relating reaction velocity to the concentration of either p21$^{H-ras}$ or the biotinylated heptapeptide are complex and sigmoidal. The inhibition curves with the various peptides differ from classic competitive inhibition curves. Finally, as mentioned in Example I, the maximal velocity of the purified enzyme is relatively low. These findings suggest that the binding of the peptides to the enzyme is not a simple equilibrium reaction. Rather, there may be a slow binding that requires conformational change.

The observation that the A1 position shows a relaxed amino acid specificity suggests that the residue at this position may not contact the farnesyl:transferase directly. Rather, the contacts may involve only the cysteine and the residues at the A2 and X positions. A working model for the active site of the farnesyl:protein transferase places the peptide substrate in an extended conformation with a largely hydrophobic pocket of the enzyme interacting with the X group of the CAAX-containing substrate.

EXAMPLE III

Recombinant Cloning of the Farnesyl:Protein Transferase Subunit Genes

This example demonstrates an approach which the inventors propose may be employed for the recombinant cloning of one or both of the farnesyl:protein transferase subunits. As will be appreciated by those of skill in the art from the following description, the preferred approach recommended by the inventors involves the application of the peptide sequence information set forth above to prepare specific primers for PCR-based sequencing, which sequences are then used for the construction of probes for screening. The specific primers proposed for use are set forth below, with reference to FIGS. 16 and 17.

A. General Methods

The inventors propose that general molecular biology techniques may be employed in connection with the cloning reactions described below (24). Where desired, cDNA clones may be subcloned into M13 and pUC vectors and sequenced by the dideoxy chain termination method (25) using the M13 universal sequencing primer or gene specific internal primers. Sequencing reactions are preferably performed using a modified bacteriophage T7 DNA polymerase (26) with $^{35}$S-labeled nucleotides, or Taq polymerase with fluorescently labeled nucleotides on an Applied Biosystems Model 370A DNA Sequencer.

For the isolation of total RNA from rat tissues, the inventors prefer to employ the guanidinium thiocyanate/CsCl centrifugation procedure (27). For the isolation of RNA from cell lines, the guanidinium HCl method is generally preferred (28). The isolation of poly A$^+$ RNA by oligo(dT)-cellulose chromatography is preferably by the procedure of Aviv and Leder (29). Northern blot hybridization using single-stranded 32P-labeled probes is generally carried out as described by Lehrman et al. (30).

B. cDNA Libraries

For the construction of a cDNA libraries, the inventors propose to employ poly A$^+$ RNA from rat brain, PC12 and/or KNRK cells. These cells are preferred in that they are believed to be rich in farnesyl:protein transferase mRNA. Although numerous convenient methods are known for the construction of cDNA libraries, the inventors believe that the use of a cDNA synthesis kit, e.g., from Invitrogen, is the most convenient. The cDNA itself is preferably prepared using both oligo(dT)- and random hexamer-primed cDNA, and then ligated to adapters, e.g., EcoR1/Not1 adapters. Next, it will generally be desirable to isolate cDNAs greater than 1 kb in size, e.g., by fractionation on a 1% agarose gel, prior to ligation to EcoR1-cleaved λgt10 DNA (Stratagene), in order to complete the construction of the cDNA-containing vectors for library preparation.

After in vitro packaging of the recombinant lambda phage with a DNA packaging extract (Stratagene), phage may be plated out on host strain *Escherichia coli* C600 hfl-cells. Typically, it will be desirable to screen approximately 1×10$^6$ plaques from the random hexamer-primer rat brain library. To carry out the screening, duplicate filters are hybridized in 6×SSC at 37° C. with about 1×10$^6$ cpm/ml of the appropriate $^{32}$P-labeled oligonucleotide probe. The polymerase chain reaction may be used to obtain an unambiguous probe for screening of the cDNA library, as well as to characterize positive λ clones, as discussed below.

The filters are washed in 6×SSC (1×SSC=150 mM NaCl, 15 mM sodium citrate, pH7) and 0.2% SDS at room temperature. DNA from colonies which remain positive after a second round of screening are purified and subcloned into a vector that is suitable for sequencing and restriction mapping, such as a bacteriophage M13 and/or pBluescript vector.

C. Polymerase Chain Reaction

1. α Subunit

To derive a sequence for constructing an appropriate probe, rat genomic DNA may be used as a template for PCR as described by Saiki et al. (31) and Lee et al. (32). The approach is to sequence a portion of the α subunit gene through the use of appropriate PCR primers (based on a consideration of the peptide sequences shown in Table I). The inventors propose to use primers that are synthesized based on the NH$_2$- and COOH-terminal sequences of peptide 2 (see Table I above), and which include the degenerate inosine base (see FIG. 16). PCR primers are end-labeled with [γ-$^{32}$P]ATP. The resultant amplified DNA fragment is then eluted and sequenced, e.g., by the Maxam-Gilbert technique (33). Translation of the nucleotide sequence between two primers should give the expected amino acid sequence of peptide 2. From this information, one may then synthesize an oligonucleotide probe that will hybridize with the region corresponding to the peptide 2 coding region, for direct screening of the library.

To characterize hybridizing λgt10 clones, plaques are eluted in 0.2 ml SM buffer (100 mM NaCl, 8 mM MgSO4, 50 mM Tris-HCl pH7.5, and 0.01% (w/v) gelatin). A primer corresponding to the right arm or left arm of λgt10 sequences flanking the unique EcoR1 site may be used in combination with a primer derived from the cDNA sequence in order to conduct a PCR amplification reaction, which may be carried out by the procedure of Saiki et al. (31). PCR products may then be analyzed on an agarose gel and the clone containing the longest insert selected and purified for further characterization.

2. β Subunit

As with the α subunit cloning, the polymerase chain reaction is used to obtain an unambiguous sequence for the peptide and to characterize positive λ clones. To derive an unambiguous sequences for the peptide, rat genomic DNA is again used as a template for PCR. In this case, though, primers are synthesized based on the NH2- and COOH-terminal sequences of peptide 7 from Table I, and include the degenerate base inosine (see FIG. 17). As above, one of the PCR primers is end-labeled with [γ-$^{32}$P]ATP. The resultant amplified DNA fragment is then eluted from acrylamide gel and sequenced. Translation of the nucleotide sequence between two primers should give the expected amino acid sequence derived from peptide. From this information, one will desire to synthesize an oligonucleotide primer for use as a hybridization probe.

D. 5' and 3' End Amplification

If one obtains a clone that is less than full length, it will, of course, be important to obtain a clone which comprises the missing sequences. This can be done through the preparation of either a 5' or 3' extended clone, depending on what is needed. To obtain an extended clone, the general procedures of Frohman et al. (34) are preferably followed that involve a combination of reverse transcription, tailing with terminal deoxytransferase and, finally, PCR.

1. 5'-End Amplification of cDNA End

Where the clone is deficient in its 5'-end, one will typically desire to carry out an 5'-end amplification, which may be carried out generally as described by Frohman et al. (34). In general, first strand cDNA is generated by reverse transcription of polyA$^+$ RNA from, e.g., either KNRK, rat brain or PC12 cells, pretreated with methyl mercury and primed with a 5'-end primer derived from the longest cDNA then available. Thus, in the case of the α subunit, one may desire to employ specific primer 1 (TGCAGTGATGTAGTTCAT), which is complementary to amino acids located towards the amino terminal of the alpha subunit.

Excess primer is removed by, e.g., application to a Amicon Centricon 100 spin filter and the first strand cDNA tailed with dATP using terminal deoxynucleotide-transferase (BRL). The reaction mixture is typically diluted to 500 µl in TE and 1- to 10-µl aliquots are used for amplification with about 10 pmol of a (dT)17-adaptor oligonucleotide which serves to prime off of the dA tail added at the 5' end of the cDNA, and about 25 pmol of a second specific primer which serves to narrow the amplification to cDNAs derived from the farnesyl:protein transferase mRNA, in 50 µl of PCR cocktail. In the case of the a subunit, the inventors propose to use the (dT)17-adaptor primer, GACTCGAGTC-GACATCGA(T)17, adaptor primer (GACTCGAGTCGA-CATCAG) and specific primer 2 (AGCGACCTCAAGA-GAACT) as the second specific primer.

The mixture is denatured (5 min, 95° C.), annealed at 52–58° C., Taq DNA polymerase added, and extended at 72° C. for 40 min. Using a DNA thermal cycler (Perkin-Elmer-Cetus), it is preferable to carry out at least 40 cycles of amplification (94° C., 40 sec; 52–58° C., 2 min; 72° C., 3 min) followed by a 15 min final extension at 72° C. Amplified PCR products may be analyzed by Southern gel analysis. The hybridizing DNA fragments are isolated and used as templates for a second PCR amplification as described above, except for the substitution of about 25 pmol of an additional specific primer 3 (such as ATGCCA-CACCGTATAGTT in the case of subunit α), which further limits the amplification to templates corresponding to the farnesyl:protein transferase cDNA. The reamplified DNA may be reprobed by Southern analysis, isolated, treated with T4 polynucleotide kinase, and cleaved with PstI for subcloning to M13 and sequencing.

2. 3'-End Amplification of cDNAs

Where resultant clones are found to be deficient in their 3' sequence, one will desire to carry out 3'-end amplification, such as described by Frohman et al. (34). For reverse transcription, KNRK cell poly(A)+ RNA may be used as a template and primed with a (dT)17-adaptor. In a 20 µl reaction mixture, 1 µg poly(A)+ RNA, 0.5 µg (dT)17-adaptor and 100 units reverse transcriptase (BRL) are incubated at 37° C. for 1 hr. Reverse transcribed cDNA is diluted 50 fold with TE (10 mM Tris-HCl, pH8.0 and 1 mM EDTA) for PCR amplification.

As an example, in the case of, e.g., the β subunit, 10 µl of diluted cDNA and 25 pmole each of adaptor primer and 17-base primer 1 (FIG. 17) are boiled, after which PCR is carried out 40 cycles of amplification (94° C., 40 sec; 58° C., 2 min; 72° C., 3 min) with TaqI polymerase. A second round of PCR is carried out as described above, except that specific primer 2 (FIG. 17) and the adapter primer are employed. Amplified PCR products are analyzed on an agarose gel, transferred to a nylon membrane and probed with $^{32}$P-labeled primer 2 (FIG. 17). The hybridizing DNA fragment is eluted, extracted with phenol/chloroform, and used as a template for a second-round PCR amplification. This amplification is carried out in same cycles as described above, except that 25 pmole each of adaptor and primer 2 is preferably substituted for primers. This reamplified DNA is then purified, cleaved with RsaI or TaqI and subcloned into, e.g., M13 vectors for sequencing.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

1. Bos, J. (1989), "ras Oncogenes in Human Cancer: A Review", *Cancer Res.*, 49:4682–4689.
2. Barbacid (1987), "ras Genes", *Ann. Rev. Biochem.*, 56:779–827.
3. Hancock, J. F., et al. (1989), "All ras proteins are polyisoprenylated but only some are palmitoylated.", *Cell*, 57:1167–1177.
4. Scheler, W. R. et al. (1989), *Science.* 248:379–385.
5. Gibbs, J. B., et al. (1989), "The ras oncogene—an important regulatory element in lower eucaryotic organisms.", *Micro Rev.*, 53:171–185.
6. Casey, P. J., et al. (1989), "p21ras is modified by a farnesyl isoprenoid," *Proc. Natl. Acad. Sci., U.S.A.*, 86:8323–8327.
7. Kamiya, Y., et al. (1978), "Structure of rhodotorucine A, a novel lipopeptide, inducing mating tube formation in *Rhodosporidium toruloides.*", *Biochem. Biophys. Res. Comm.*, 83:1077–1083.
8. Kamiya, Y., et al. (1979), *N. Agric. Biol. Chem.*, 43:1049–1053.
9. Sakagami, Y., et al. (1981), "Peptidal sex hormones inducing conjugation tube formation in compatible mating type cells of *Tremella-mesenterica.*", *Science*, 212:1525–1527.
10. Gutierrez, L., et al. (1989), "Post-translational processing of p21ras is two-step and involves carboxymethylation and carboxy-terminal proteolysis.", *Embo J.*, 8:1093–1098.
11. Lowry, D. R. et al. (1989), *Nature*, 341: 384–385.
12. Clarke, E., et al. (1988), "Posttranslational modification of the Ha-ras oncogene protein: evidence for a third class of protein carboxyl methyltransferases.", *Proc. Natl. Acad. Sci. U.S.A.*, 85:4643–4647.
13. Davisson, V. J., et al. (1986), "Phosphorylation of isoprenoid alcohols.", *J. Org. Chem.*, 51:4768–4779.
14. Feig, L. A., et al. (1986), "Isolation of ras GTP-binding mutants using an in situ colony-binding assay.", *Proc. Natl. Acad. Sci. U.S.A.*, 83:4607–4611.
15. Farnsworth, D. C., et al. (1989), "Human lamin B contains a farnesylated cysteine residue.", *J. Biol. Chem.*, 264:20422–20429.
16. Laemmli, U. K. (1970), "Cleavage of structural proteins during the assembly of the head of bacteriophage T4.", *Nature*, 227:680–685.
17. Lowry, O. H., et al. (1951), *J. Biol. Chem.*, 193:265–275.
18. Stewart, J. M. et al. (1984), *Solid Phase Peptide Synthesis*, 2nd ed., Pierce Chemical Co., Rockford, Ill.
19. Akada, R., et al. (1989), *Mol. Cell. Biol.*, 9:3491–3498.
20. Gautam, N., et al. (1989), *Science*, 244:971–974.
21. Robishaw, J. D., et al. (1989), *J. Biol. Chem.*, 264:15758–15761.
22. Yamane, H. K., et al. (1990), *Proc. Natl. Acad. Sci. USA*, 87:5868–5872.
23. Mumby, S. M., et al. (1990), *Proc. Natl. Acad. Sci. USA*, 87:5873–5877.
24. Sambrook, J., et al. (1989), *Molecular Cloning: A Laboratory Manual*, Cold Spring Harbor Laboratory, Cold Spring Harbor, N.Y.

25. Sanger, F., et al. (1977), *Proc Natl. Acad. Sci. USA,* 74:5463–5467.
26. Tabor, S., et al. (1987), *Proc Natl. Acad. Sci. USA,* 844767–4771.
27. Glisin, V., et al. (1974), *Biochemistry,* 13:2633–2640.
28. Chirgwin, J. M., et al. (1979), *Biochemistry,* 18:5294–5303.
29. Aviv, H., et al. (1972), *Proc. Natl. Acad. Sci. USA,* 69:1408–1412.
30. Lehrman, M. A., et al. (1987), *J. Biol. Chem.,* 262:3354–3361.
31. Saiki, R. K., et al. (1988), *Science,* 239:487–491.
32. Lee, C. C., et al. (1988), *Science,* 239:1288–1291.
33. Maxam, A. M., et al. (1980), *Methods Enzymol.,* 65:499–560.
34. Frohman, M. A., et al. (1988), *Proc. Natl. Acad. Sci. USA,* 85:8998–9002.

What is claimed is:

1. A method for assaying for the presence of farnesyl transferase activity in a composition comprising (a) obtaining a composition suspected of having farnseyl transferase activity, which activity transfers a farnesyl moiety to a farnesyl acceptor protein or peptide; and (b) testing the composition for activity in catalyzing the transfer of a farnesyl moiety to a farnesyl acceptor protein or peptide, wherein such activity indicates the presence of farnesyl transferase in said composition.

2. The method of claim 1, wherein said farnesyl moiety is transferred from farnesyl pyrophosphate.

3. The method of claim 2, wherein said farnesyl pyrophosphate contains a label on the farnesyl moiety.

4. The method of claim 1, wherein said farnesyl acceptor protein or peptide comprises a carboxy terminal sequence of -C-A-A-X, wherein:

C=cysteine;

A=an aliphatic or hydroxy amino acid; and

X=any amino acid.

5. The method of claim 4, wherein said farnesyl acceptor protein or peptide comprises a p21$^{ras}$ protein.

6. The method of claim 4, wherein said farnesyl acceptor protein or peptide comprises a peptide of at least 4 amino acids in length.

7. The method of claim 6, wherein the farnesyl acceptor protein or peptide comprises CVIM; KKSKTKCVIM; TKCVIM; RASNRSCAIM; TQSPQNCSIM; CIIM; CVVM; or CVLS.

* * * * *